United States Patent
Badri et al.

(10) Patent No.: US 9,078,946 B2
(45) Date of Patent: Jul. 14, 2015

(54) METHODS OF SURFACE TREATING POROUS PARTICLES

(75) Inventors: Brinda B. Badri, Woodbury, MN (US); Moses M. David, Woodbury, MN (US); Haoming Rong, Woodbury, MN (US); Badri Veeraraghavan, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 52 days.

(21) Appl. No.: 13/504,984

(22) PCT Filed: Nov. 23, 2010

(86) PCT No.: PCT/US2010/057799
§ 371 (c)(1),
(2), (4) Date: Apr. 30, 2012

(87) PCT Pub. No.: WO2011/063392
PCT Pub. Date: May 26, 2011

(65) Prior Publication Data
US 2012/0219728 A1 Aug. 30, 2012

Related U.S. Application Data

(60) Provisional application No. 61/263,573, filed on Nov. 23, 2009, provisional application No. 61/263,580, filed on Nov. 23, 2009.

(51) Int. Cl.
| | |
|---|---|
| *B05D 5/00* | (2006.01) |
| *H05H 1/24* | (2006.01) |
| *A61L 15/42* | (2006.01) |
| *A61F 13/42* | (2006.01) |
| *A61F 13/84* | (2006.01) |
| *A61L 15/46* | (2006.01) |
| *B01J 20/24* | (2006.01) |
| *B01J 20/26* | (2006.01) |
| *B01J 20/28* | (2006.01) |
| *B01J 20/32* | (2006.01) |

(52) U.S. Cl.
CPC ............. *A61L 15/425* (2013.01); *A61F 13/42* (2013.01); *A61F 13/8405* (2013.01); *A61L 15/46* (2013.01); *B01J 20/24* (2013.01); *B01J 20/267* (2013.01); *B01J 20/28004* (2013.01); *B01J 20/28028* (2013.01); *B01J 20/28078* (2013.01); *B01J 20/3204* (2013.01); *B01J 20/3208* (2013.01); *B01J 20/3246* (2013.01); *A61L 2300/606* (2013.01); *B01J 2220/42* (2013.01); *B01J 2220/46* (2013.01); *B01J 2220/49* (2013.01)

(58) Field of Classification Search
None
See application file for complete search history.

(56) References Cited

U.S. PATENT DOCUMENTS

| | | |
|---|---|---|
| 3,746,655 A | 7/1973 | Urbanic |
| 4,054,689 A | 10/1977 | Calvin |
| 4,694,092 A | 9/1987 | Takahata et al. |
| 4,732,805 A | 3/1988 | Maggs |
| 5,082,575 A | 1/1992 | Yamaguchi |
| 5,364,382 A | 11/1994 | Latimer et al. |
| 5,407,442 A | 4/1995 | Karapasha |
| 5,490,846 A | 2/1996 | Ellis et al. |
| 5,521,008 A | 5/1996 | Lieberman et al. |
| 5,637,105 A | 6/1997 | Tanaka et al. |
| 5,698,217 A | 12/1997 | Wilking |
| 5,743,942 A | 4/1998 | Shelley et al. |
| 5,817,704 A | 10/1998 | Shiveley et al. |
| 6,015,597 A | 1/2000 | David |
| 6,197,120 B1 | 3/2001 | David |
| 6,214,255 B1 | 4/2001 | Hekal |
| 6,281,407 B1 | 8/2001 | Warner et al. |
| 6,450,997 B1 | 9/2002 | Seitz et al. |
| 6,482,867 B1 * | 11/2002 | Kimura et al. ............... 521/149 |
| 6,503,525 B1 | 1/2003 | Paul et al. |
| 6,649,222 B1 | 11/2003 | D'Agostino et al. |

(Continued)

FOREIGN PATENT DOCUMENTS

| | | |
|---|---|---|
| CN | 1800013 | 7/2006 |
| JP | S55-23039 A | 2/1980 |

(Continued)

OTHER PUBLICATIONS http://www.waters.com/waters/en_US/HPLC-Separation-Modes/nav.htm?cid=10049076&locale=en_US, Author unknown, Mar. 19, 2008, published by Waters Co., No volume, no issue number, 6 pages.*
http://www.google.com/search?q=water+is+retained+in+the+pores+when+placed+in+organic+liquid&rls=com.microsoft%3Aen-us%3AIE-SearchBox&biw=1200&bih=588&sa=X&ei=jyW9UdvPGYjl0gGlyoCIDA&ved=0CBwQpwUoBg&source=lnt&tbs=cdr%03A1%02Ccd_min%3A1%2F1%2F1900%2Ccd_max%3A11%2F23%2F2008&tbm=, No author, journal, volume, or issue, 2 pages in length.*

(Continued)

*Primary Examiner* — Robert M Kelly
(74) *Attorney, Agent, or Firm* — James A. Baker

(57) ABSTRACT

A method of treating porous particles, each porous particle having an external surface and a multiplicity of pores with interior pore surfaces, by contacting the external surface with a hydrophobic agent while causing the interior pore surfaces to remain substantially free of the hydrophobic agent. In certain illustrative embodiments, treating the external surfaces of the porous particles includes exposing the porous particles to at least one of water vapor, methanol vapor, or ethanol vapor; and subsequently exposing the porous particles to a second vapor comprising a reactive organosilane compound which reacts to form the hydrophobic agent. In some particular illustrative embodiments, at least a portion of the external surface of the treated porous particle includes hydrophobic groups, the hydrophobic groups selected from at least one of alkyl or aryl groups optionally substituted with fluorine, and siloxanes having alkyl groups, aryl groups, or combinations thereof.

20 Claims, 5 Drawing Sheets

(56) References Cited

U.S. PATENT DOCUMENTS

| | | |
|---|---|---|
| 6,664,439 B1 | 12/2003 | Arndt et al. |
| 6,740,406 B2 | 5/2004 | Hu et al. |
| 6,878,419 B2 | 4/2005 | David et al. |
| 7,148,396 B2 | 12/2006 | Cohen et al. |
| 7,169,720 B2 | 1/2007 | Etchells et al. |
| 7,205,259 B2 | 4/2007 | Soerens |
| 2003/0032681 A1 | 2/2003 | Coronado et al. |
| 2003/0124564 A1 | 7/2003 | Trau et al. |
| 2004/0122389 A1 | 6/2004 | Mace et al. |
| 2005/0123763 A1 | 6/2005 | Hiltzik et al. |
| 2006/0244034 A1 | 11/2006 | Sakurai et al. |
| 2008/0053891 A1 | 3/2008 | Koops et al. |
| 2009/0180967 A1 | 7/2009 | Tu et al. |

FOREIGN PATENT DOCUMENTS

| | | |
|---|---|---|
| JP | S62-176912 A | 8/1987 |
| JP | 2002-509763 | 4/2002 |
| JP | 2006-308898 A | 11/2006 |
| JP | 2007-138003 A | 6/2007 |
| JP | 2010-18447 A | 1/2010 |
| JP | 2010-195604 A | 9/2010 |
| WO | 99/49824 | 10/1999 |
| WO | WO 2008/000457 A | 1/2008 |
| WO | WO 2009/012116 | 1/2009 |
| WO | WO 2011/063370 | 5/2011 |
| WO | WO 2011/063372 | 5/2011 |

OTHER PUBLICATIONS

Hersey, "Ordered Mixing: A New Concept in Powder Mixing Practice", *Powder Technology*, vol. 11, (1975), pp. 41-44.

Tripp et al., "An Infrared Study of the Reaction of Octadecyltrichlorosilane with Silica", *Langmuir*, vol. 8, 1992, pp. 1120-1126.

Tripp et al., "Reaction of Alkylchlorosilanes with Silica at the Solid/Gas and Solid/Liquid Interface", *Langmuir*, vol. 8, 1992, pp. 1961-1967.

Tripp et al., "Effect of Fluoroalkyl Substituents on the Reaction of Alkylchlorosilanes with Silica Surfaces", *Langmuir*, vol. 9, 1993, pp. 3518-3522.

Tripp et al., "Reaction of Methylsilanols with Hydrated Silica Surfaces: The Hydrolysis of Trichloro-, Dichloro-, and Monochloromethylsilanes and the Effects of Curing", *Langmuir*, vol. 11, 1995, pp. 149-155.

Belyakova et al., "Surfaces properties of silica gels modified with hydrophobic groups", *Colloids and Surfaces A: Physicochemical and Engineering Aspects*, vol. 154, 1999, pp. 285-294.

Furukawa et al., "Formation of silica gel surfaces having lipophobic and hydrophobic characters by a radio-frequency $CF_4$ plasma treatment", *Journal of Materials Science Letters*, 19, 2000, pp. 1545-1547.

Pfeffer et al., "Synthesis of engineered particulates with tailored properties using dry particle coating", *Powder Technology*, vol. 117, (2001), pp. 40-67.

Lazghab et al., "Wettability assessment of finely divided solids", *Powder Technology*, vol. 157, 2005, pp. 79-91.

Shen et al., "Surface Chemical Functional Groups Modification of Porous Carbon", *Recent Patents on Chemical Engineering*, vol. 1, (2008), pp. 27-40.

ASTM D2854-09, "Standard Test Method for Apparent Density of Activated Carbon", 3 pages.

ASTM D3467-04 (2009), "Standard Test Method for Carbon Tetrachloride Activity of Activated Carbon", 3 pages.

\* cited by examiner

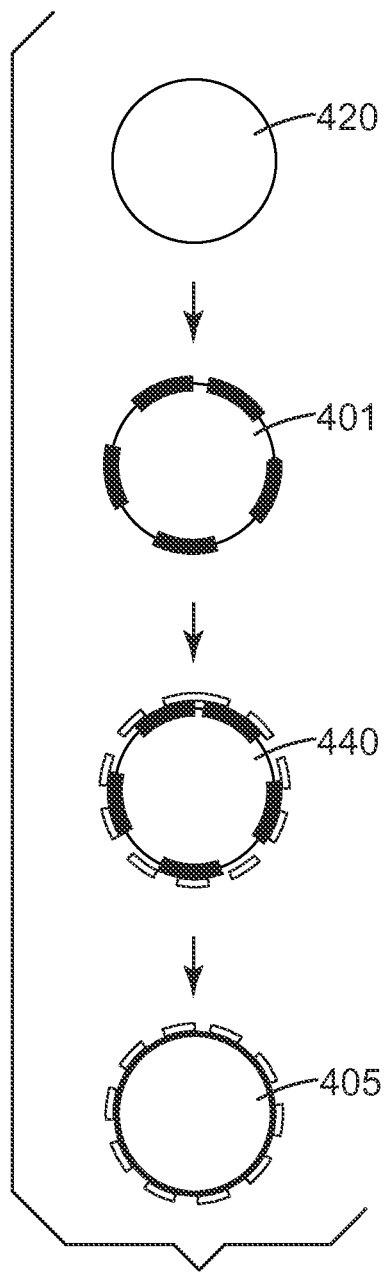
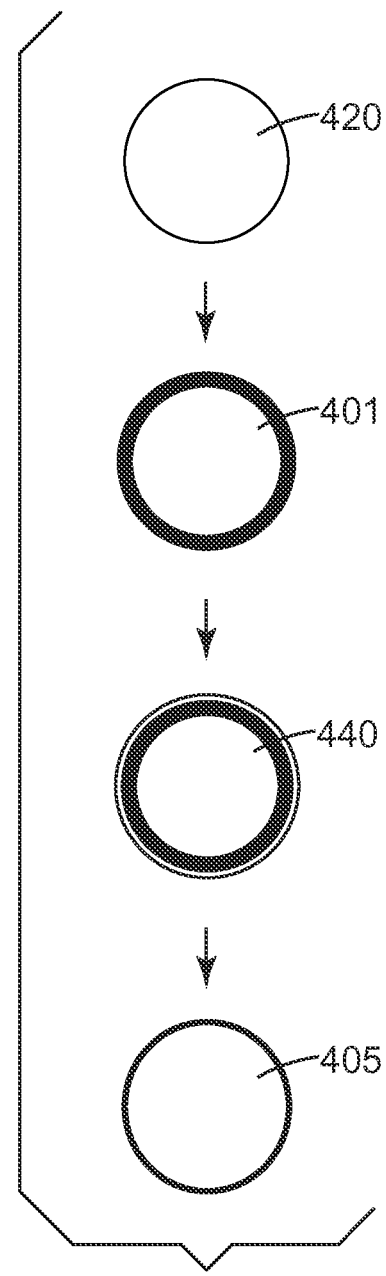
*Fig. 4C*  *Fig. 4D*

METHODS OF SURFACE TREATING POROUS PARTICLES

CROSS REFERENCE TO RELATED APPLICATION

This application claims the benefit of U.S. Provisional Patent Application No. 61/263,573, filed Nov. 23, 2009, and 61/263,580, filed Nov. 23, 2009, the disclosures of which are incorporated by reference herein in their entirety.

TECHNICAL FIELD

The present disclosure relates to methods of treating porous particles, and more particularly, methods of selectively altering the hydrophilicity of exterior surfaces of porous particles.

BACKGROUND

Certain porous particles have a wide variety of uses in the chemical arts. For example, hydrophobic oxide materials are widely used for different gas- and liquid-phase separation processes. A particularly widely used example is silica gel, which is known to be useful for many applications including chromatography, adsorption and purification of biologically active compounds and medicinal preparations, and stabilization of multi-component systems. However, the surface properties of native silica are not always appropriate for the desired application. Surface modification can be achieved, for example, by transformation of hydrophilic silanol groups into hydrophobic groups, which generally lowers the affinity of modified silica with respect to water. In general, known hydrophobic treatments of silica gel are designed to make both the external surface and the internal pore surface hydrophobic.

SUMMARY

In one aspect, the disclosure describes a method of treating a plurality of porous particles. The method comprises providing a plurality of porous particles, each porous particle having an external surface and a plurality of pores with interior pore surfaces, and treating the external surfaces of the porous particles by contacting the external surfaces with a hydrophobic agent while causing the interior pore surfaces to remain substantially free of the hydrophobic agent. In some exemplary embodiments, treating the external surface of the porous particle comprises forming a layer comprising silicon, hydrogen, and carbon on at least a portion of the external surface of the porous particle by plasma deposition. In certain such embodiments, the method further comprises forming a layer comprising fluorine and carbon by plasma deposition on at least the portion of the layer comprising silicon, hydrocarbon, and carbon.

In additional exemplary embodiments of the foregoing aspect and embodiments, treating the external surfaces of the porous particle comprises exposing the porous particles to at least one of water vapor, methanol vapor, or ethanol vapor, and exposing the porous particles to a second vapor comprising a reactive organosilane compound which reacts to form the hydrophobic agent. In some exemplary embodiments, exposing the porous particles to at least one of water vapor, methanol vapor, or ethanol vapor takes place before exposing the porous particles to the second vapor comprising the reactive organosilane compound.

In certain such embodiments, at least a portion of the water vapor, methanol vapor, or ethanol vapor condenses within at least a portion of the plurality of pores of the porous particles, thereby at least partially occluding the interior pore surfaces, before exposing the porous particles to the second vapor comprising the reactive organosilane compound. In additional such embodiments, the method further comprises substantially removing the condensed water vapor, methanol vapor, or ethanol vapor from the pores after exposing the porous particles to the second vapor comprising the reactive organosilane compound, optionally wherein substantially removing the condensed water vapor, methanol vapor, or ethanol vapor from the pores is accomplished by heating the particles, exposing the particles to a vacuum, or a combination thereof.

In some exemplary embodiments of the foregoing aspect and embodiments, the method further comprises exposing the porous particles to a third vapor comprising a volatile compound non-reactive with the reactive organosilane before exposing the porous particles to the at least one of water vapor, methanol vapor, or ethanol vapor and the second vapor, wherein at least a portion of the volatile compound condenses within at least a portion of the plurality of pores of the porous particles, thereby at least partially occluding the interior pore surfaces. In some such exemplary embodiments, the volatile compound is selected from the group consisting of molecular nitrogen, carbon dioxide, a $C_1$-$C_2$ hydrocarbon, and combinations thereof. In certain such exemplary embodiments, the method further comprises substantially removing the condensed volatile compound from the pores after exposing the porous particles to the second vapor comprising the reactive organosilane compound, optionally wherein substantially removing the condensed volatile organic compound from the pores is accomplished by heating the particles, exposing the particles to a vacuum, or a combination thereof.

In certain of the foregoing embodiments which comprise treating the external surfaces of the porous particle by exposing the porous particles to at least one of water vapor, methanol vapor, or ethanol vapor, at least a portion of the water vapor, methanol vapor, or ethanol vapor reacts with at least a portion of the reactive organosilane compound in a vapor phase outside of the pores of the porous particles.

In some particular examples of such embodiments which comprise treating the external surfaces of the porous particle by exposing the porous particles to at least one of water vapor, methanol vapor, or ethanol vapor, the reactive organosilane compound comprises at least two silane functional reactive groups. In further examples of such embodiments, the reactive organosilane compound is selected from dichlorodimethylsilane and dichlorodiethylsilane. In additional examples of such embodiments, the reactive organosilane compound has a vapor pressure at 25° C. of from 133 Pa to 26,600 Pa. In certain presently preferred embodiments, treating the external surface of the porous particle takes place at a total vapor pressure of from 1,330 to 26,600 Pa.

In other examples of any of the foregoing aspect and embodiments, the plurality of pores exhibit a median pore size of at least 1 nm and no more than 4 nm, and further wherein exposing the porous particle to the second vapor comprising the reactive organosilane compound occurs at a total vapor pressure of from 1,330 to 19,950 Pa. In some particular presently preferred embodiments, the plurality of pores exhibits a median pore size of at least 4 nm and no more than 10 nanometers, and further wherein exposing the porous particle to the second vapor comprising the reactive organosilane compound occurs at a total vapor pressure of from 6,650 to 26,600 Pa.

In any of the foregoing aspect and embodiments, the porous particles are selected from the group consisting of porous inorganic particles, porous organic particles, porous metal particles, porous (co)polymeric particles, porous carbon particles, porous clay particles, porous molecular sieve particles, porous zeolite particles, porous desiccant particles, and combinations thereof.

In any of the foregoing aspect and embodiments, at least a portion of the external surface of the treated porous particle comprises hydrophobic groups, the hydrophobic groups comprising at least one of alkyl or aryl groups, further wherein the alkyl and aryl groups are each optionally substituted with fluorine, and additionally wherein the interior pore surfaces are at least partially hydrophilic. In some such embodiments, the hydrophobic groups comprise siloxanes having alkyl groups, aryl groups, or combinations thereof.

Thus, in some exemplary embodiments, the present disclosure describes a method of making treated porous particle comprising an external surface and interior pore surfaces, wherein at least a substantial portion of the external surface of the treated porous particle comprises a hydrophobic group, and wherein the interior pore surfaces are substantially untreated. In certain exemplary embodiments, the hydrophobic groups comprise at least one of alkyl or aryl groups, wherein alkyl and aryl are each optionally substituted with fluorine. In some exemplary embodiments, the treated porous particle is a treated desiccant particle. In some such embodiments, the treated porous particle is a treated silica gel particle, a treated montmorillonite clay particle, a treated molecular sieve, or a treated activated carbon particle. In certain exemplary embodiments, the hydrophobic groups comprise siloxanes having alkyl groups, aryl groups, or combinations thereof. In some particular exemplary embodiments, the treated porous particle is a silica gel particle with an external surface having up to 5 atomic percent silicon atoms up to a depth of 50 angstroms, as determined by x-ray photoelectron spectroscopy.

The present disclosure also describes methods of making a treated porous particle comprising an external surface and interior pore surfaces, wherein at least a portion of the external surface of the treated porous particle comprises hydrophobic groups, the hydrophobic groups comprising at least one of alkyl or aryl groups, wherein the alkyl and aryl groups are substituted with fluorine, and wherein the interior pore surfaces are at least partially hydrophilic. In some exemplary embodiments, the treated porous particle is a treated desiccant particle. In some such embodiments, the treated porous particle is a treated silica gel particle, a treated montmorillonite clay particle, a treated molecular sieve, or a treated activated carbon particle. In some particular exemplary embodiments, the hydrophobic groups comprise siloxanes having alkyl groups, aryl groups, or combinations thereof. In some exemplary embodiments, the treated porous particle is a silica gel particle with an external surface having up to 5 atomic percent silicon atoms up to a depth of 50 angstroms, as determined by x-ray photoelectron spectroscopy.

In some particular exemplary embodiments, the plurality of particles further comprises untreated desiccant particles (e.g., silica gel, montmorillonite clay, molecular sieves, or activated carbon). In certain particular exemplary embodiments, the plurality of particles is substantially free of particles wherein the external surface and the interior pore surfaces are both treated with hydrophobic groups. In other particular exemplary embodiments, the plurality of particles further comprises absorbent particles or fibers comprising at least one of superabsorbent polymers, hydrophilic nonwovens, or wood pulp.

In another aspect, the present disclosure provides a method of making a treated porous particle according to any one of the foregoing embodiments, the method comprising treating an external surface of a porous particle with a hydrophobic agent while allowing interior pore surfaces of the porous particle to remain substantially untreated. In some exemplary embodiments, only the external surface of the porous particle is treated with the hydrophobic agent.

In a further aspect, the present disclosure describes treated porous particles having hydrophobic groups on the external surface and a hydrophilic interior and methods of making them. The treated porous particles may be useful, for example, as desiccants for controlling humidity within the environment of an absorbent article. Absorbent articles (e.g., sanitary pads and diapers) typically contain superabsorbent polymers (SAP) and/or wood pulp in the core region to absorb and retain fluid. Treated particles disclosed herein in the presence of SAP or wood pulp are shown to decrease the humidity in an environment similar to that adjacent the skin of the user of an absorbent article.

While it is known to incorporate desiccants (e.g., silica gel) into components of absorbent articles to reduce the relative humidity of the environment adjacent the skin of a wearer, when these desiccants are exposed to aqueous liquids, their efficacy is diminished or inconsistent, and they tend to cause a slippery or slimy feeling for the wearer of the absorbent article. It is known to encapsulate desiccants in a pouch made of material that can allow the penetration of moisture vapor and exclude aqueous liquids (e.g., microporous films made with thermally induced phase separation or particle filled membranes). Placing such pouches in the absorbent article may require special process techniques and may therefore be undesirable. The treated porous particles disclosed herein typically repel aqueous liquids and are shown in the present disclosure to reduce the relative humidity near the wearer's skin more consistently and reliably than untreated desiccant particles. They can be added to absorbent articles without the use of pouches or other cumbersome physical isolation techniques.

Various aspects and advantages of exemplary embodiments of the exemplary embodiments of the present disclosure have been summarized. The above Summary is not intended to describe each illustrated embodiment or every implementation of the exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying drawings, in which:

FIGS. 4A-4D are schematic representations of exemplary methods of surface treating porous particles and the resulting treated porous particles according to some illustrative embodiments of the present disclosure.

DETAILED DESCRIPTION

Glossary

Figure 1:
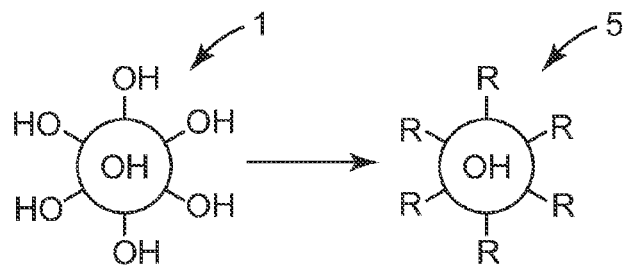
FIG. 1 is a schematic representation of an exemplary method of surface treating porous particles and the resulting treated porous particles according to some illustrative embodiments of the present disclosure.

Throughout this application:

Terms such as "a", "an" and "the" are not intended to refer to only a singular entity, but include the general class of which a specific example may be used for illustration. The terms "a", "an", and "the" are used interchangeably with the term "at least one".

The phrase "at least one of" followed by a list of two or more items refers to any one of the items in the list and any combination of two or more items in the list.

"Hydrophilic" describes surfaces that are wettable by aqueous liquids (i.e., liquids comprising water) in contact with the surfaces. Wettability can be measured by contact angle of the liquid on the surface. Typically, a surface is hydrophilic when the contact angle of water on the surface is less than 90°.

"Hydrophobic group" describes functional groups that render surfaces nonwettable by aqueous liquids (i.e., liquids comprising water) in contact with the surfaces. Typically, a surface is hydrophobic when the contact angle of water on the surface is greater than 90°.

"At least a portion of the external surface" and "at least a substantial portion of the external surface" can include uniform or non-uniform distribution of hydrophobic groups on the external surface of the particle. In some exemplary embodiments, hydrophobic groups are uniformly distributed on the external surface of the particle. In some exemplary embodiments, the entire external surface of the particle is covered by hydrophobic groups.

"Desiccant" refers to a material that can absorb moisture from a surrounding atmosphere. Desiccants as used herein can absorb water or water vapor by physical absorption into the porous structure.

The term "absorbent component", refers to a component generally used as the primary absorbent component of an absorbent article, such as the absorbent core of the absorbent article. It also includes absorbent components, such as the secondary topsheets described herein that serve a wicking or storage function. The term absorbent component, however, excludes components that are generally only used as the topsheet or backsheet of the absorbent article.

"Disposable" is generally understood to mean something that has a limited period of use before its ability to perform its intended function is exhausted. With regard to garments, "disposable" garments typically are not constructed to withstand laundering.

Aqueous means including water. The term "aqueous fluids" encompasses biological fluids.

"Alkyl group" and the prefix "alk-" are inclusive of both straight chain and branched chain groups and of cyclic groups. Unless otherwise specified, alkyl groups herein have up to 20 carbon atoms. Cyclic groups can be monocyclic or polycyclic and, in some exemplary embodiments, have from 3 to 10 ring carbon atoms. "Alkylene" is the divalent form of "alkyl".

The term "fluoroalkyl" includes linear, branched, and/or cyclic alkyl groups in which all C—H bonds are replaced by C—F bonds as well as groups in which hydrogen or chlorine atoms are present instead of fluorine atoms provided that up to one atom of either hydrogen or chlorine is present for every two carbon atoms. In some exemplary embodiments of fluoroalkyl groups, when at least one hydrogen or chlorine is present, the fluoroalkyl group includes at least one trifluoromethyl group. The term "perfluoroalkyl group" includes linear, branched, and/or cyclic alkyl groups in which all C—H bonds are replaced by C—F bonds.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

"Alkylarylene" refers to an "arylene" moiety to which an alkyl group is attached.

"Plasma treatment" refers to a process where high frequency electric or magnetic fields are used to create free radicals of a particular gas in an atmosphere where a porous particle is present. The free radicals modify the surface of the porous particles. The term "plasma treatment" can encompass "plasma deposition", in which a film formed from the plasma is deposited on at least a portion of the surface and is generally attached to the surface through covalent bonds.

Various exemplary embodiments of the disclosure will now be described with particular reference to the Drawings. Embodiments of the present disclosure may take on various modifications and alterations without departing from the spirit and scope of the disclosure. Accordingly, it is to be understood that the embodiments of the present disclosure are not to be limited to the following described exemplary embodiments, but is to be controlled by the limitations set forth in the claims and any equivalents thereof.

Porous Particles

A schematic illustration of treating a porous particle 1 and a treated porous particle 5 according to some embodiments of the present disclosure is shown in FIG. 1. In the illustrated embodiment, porous particle 1 has a hydrophilic external surface and hydrophilic interior pore surfaces. The hydrophilic external surface and interior pore surfaces are hydrophilic in this embodiment because of the multiple hydroxyl (—OH) groups, which in the illustration are shown on the external surface and inside of the circle representing porous particle 1. When porous particle 1 is treated with a hydrophobic agent using a method according to the present disclosure, treated porous particle 5 is formed. In the illustrated embodiment, treated porous particle 5 has a hydrophobic external surface, which is represented by multiple hydrophobic groups (R) on the external surface. Treated porous particle 5, however, remains hydrophilic on its interior pore surfaces, which again is represented by the hydroxyl group shown on the inside of the circle representing treated porous particle 5.

In any of the embodiments of treated porous particles 5 according to the present disclosure, at least a portion of the external surface of the treated porous particle comprises hydrophobic groups R. Exemplary R groups include alkyl groups and fluoroalkyl groups having up to 20, 18, 15, 12, 10, or 8 carbon atoms (e.g., in a range from 1 to 20, 1 to 15, 1 to 10, 1 to 5, or 1 to 3 carbon atoms). Further examples of R groups include aryl, arylalklyenyl, or alkylarylenyl groups, each of which may be substituted with one or more fluoro groups. In some exemplary embodiments, the R groups include at least one of methyl, trifluoromethyl, difluoromethyl, or fluoromethyl groups. In some exemplary embodiments, hydrophobic group R comprises siloxanes having alkyl groups, aryl groups, arylalkylenyl (e.g., benzyl) groups, alkylarylenyl groups, or combinations thereof. In some of these embodiments, the treated porous particle 5 is a treated silica gel particle. The alkyl groups on the siloxanes have up to 20, 18, 15, 12, 10, or 8 carbon atoms (e.g., in a range from 1 to 20, 1 to 15, 1 to 10, 1 to 5, or 1 to 3 carbon atoms) and may optionally be substituted with one or more fluoro groups.

Typically, a major portion (e.g., greater than 50 or at least 51, 55, 60, 65, 70, 75, 80, 85, 90, or 95 percent) of the external surface area is covered by hydrophobic groups. In some exemplary embodiments, a substantial portion (e.g., at least 90, 95, 96, 97, 98, or 99 percent up to 100 percent) of the external surface comprises hydrophobic groups. Techniques for analyzing the external surface coverage of a particle are known in the art (e.g., infrared, raman, and nuclear magnetic resonance spectroscopy); see, e.g., L. A. Belyakova et al., *Colloids and Surfaces A: Physicochemical and Engineering Aspects*, 154, 285-294 (1999).

The external surface of a particle can also be analyzed by electron spectroscopy chemical analysis (ESCA). ESCA can be used to report the atomic percent of various elements on a surface. The results depend, for example, on the particular hydrophobic groups on the surface and the method of applying them to the surface. In some exemplary embodiments, a substantial portion of the external surface comprising hydrophobic groups refers to elements making up the porous particle being absent on the surface as determined by ESCA. In some exemplary embodiments (e.g., embodiments where the treated porous particle 5 is a treated silica gel particle) the external surface is free of silicon atoms up to a depth of 50 angstroms, as determined by x-ray photoelectron spectroscopy.

The external surface of a particle can also be analyzed by time-of-flight secondary ion mass spectrometry (TOF-SIMS). TOF-SIMS can be used to detect chemical compositions on a surface, usually with a depth range from 5 to 20 angstroms. The results depend, for example, on the particular hydrophobic groups on the surface and the method of applying them to the surface. Relative quantification is possible with SIMS, typically by taking a ratio of counts for a mass of interest over counts for a reference ion or counts for a mass of interest over total spectrum integrated counts.

Typically, a treated porous particle 5 disclosed herein has a substantial portion of its external surface comprising hydrophobic groups when the treated porous particle floats on the surface of water. When the surface tension force of a liquid is high enough to balance the gravitational force on a particle at the gas/liquid interface, the particle is said to float on the surface. When treated porous particles 5 according to the present disclosure are sprinkled on the surface of water, the wettability of the treated porous particles 5 may correlate with the time it takes for the particles to sink.

In some exemplary embodiments, the treated porous particle 5 remains on the surface of the water indefinitely. In some exemplary embodiments, the treated porous particle 5 remains on the surface of the water for at least 8 hours, 6 hours, 4 hours, 2 hours, or 30 minutes. The floating particle method is a technique known in the art for evaluating the surface wettability of particles; (see, e.g., M. Lazghab et al., *Powder Technology*, 157, 83 (2005). The hydrophobicity of the external surfaces of a plurality of treated porous particles 5 according to the present disclosure can be evaluated by sprinkling the treated porous particles 5 on a surface of water to form a single layer.

Typically, at least 75 percent (in some exemplary embodiments, 80, 85, 90, or at least 95 percent) of the particles float on the surface of the water. In some exemplary embodiments, the evaluation can be carried out by placing one gram of treated porous particles on the surface of 10 milliliters (mL) of water in a 20-mL vial and observing whether the particles float on the surface. When a vial containing the treated particles and water is shaken, the particles typically agglomerate. With time, they typically break apart and re-floated in water. There is typically no such clump formation observed when untreated hydrophilic particles are shaken in water. Instead untreated hydrophilic particles typically sink in water.

Not all hydrophobic treatments provide particles that float on the surface of water. For example, some hydrophobic treatments (e.g., when surface hydroxyl groups are replaced with fluorine by plasma treatment) may hydrolyze upon contact with liquid water. It has now been observed that particles treated with $NF_3$ plasma do not float on the surface of water but instead sink into the water. The present disclosure provides hydrophobic treatments that are robust and do not hydrolyze when they are placed on the surface of water.

The hydrophobic nature of the treated porous particles 5 according to the present disclosure can also be evaluated, for example, using contact angle measurements on individual particles or bulk particles using techniques known in the art. In some exemplary embodiments, the contact angle of a water droplet on the treated porous particles 5 is at least 120, 110, 100, or 95 degrees (e.g., in a range from 90 to 100 degrees, 95 to 110 degrees, 100 to 115 degrees, 110 to 130 degrees, or 115 to 125 degrees).

In any of the embodiments of treated porous particles 5 according to the present disclosure, the interior pore surfaces of the treated porous particle 5 are at least partially hydrophilic. In some exemplary embodiments, the interior pore surfaces of the treated porous particles 5 are said to be hydrophilic when they have hydrophilic functional groups. Hydrophilic functional groups typically include hydroxyl, silanol groups, or other metal oxide groups depending on the nature of the particle. In some exemplary embodiments, when the porous particles 1 have interior pore surfaces that include hydroxyl or silanol groups, the treated porous particles 5 have at least 50, 60, 70, 75, 80, 85, or 90 percent of the hydroxyl or silanol groups that were present in the porous particles 1 before treatment.

Methods for evaluating the interior pore surfaces of porous particles are known in the art. For example, absorption techniques (e.g., using methanol, ethanol, water, benzene, or nitrogen) are commonly used. Since a large percentage of surface area in porous particles is in the interior pore surfaces, large changes in absorption typically result when the wettability of the interior pore surfaces is altered. The interior pore surfaces can be said to be "substantially untreated", for example, when the treated porous particles 5 have at least 90, 95, 96, 97, or 98 percent of the hydroxyl or silanol groups that were present in the porous particles 1 before treatment, as measured using common absorption techniques. Porous particles may also be cross-sectioned and their interior chemical compositions analyzed using ESCA or TOF-SIMS as described above.

Thus in some exemplary embodiments, minimal to no hydrophobic groups are observed on the interior of the treated porous particles using these techniques. In these embodiments, the interior pore surfaces are said to be "substantially untreated". In some exemplary embodiments, the interior pore surfaces of the treated porous particles disclosed herein have minimal to no alkyl or aryl groups, optionally substituted with fluorine, as evidenced by TOF-SIMS. In the case of TOF-SIMS, relative quantification of hydrophobic to hydrophilic functional groups is possible, typically by taking a ratio of counts for a mass of a hydrophobic group over counts for a hydrophilic group. Ratios of counts from the external surface can be compared to ratios of counts from the interior surface.

In certain presently preferred exemplary embodiments, the treated porous particles 5 disclosed herein absorb at least 20 (in some exemplary embodiments at least 22, 25, 28, 30, or 32) percent of their weight of water vapor after 24 hours at 30° C. and 50 percent relative humidity. Generally, this absorption is carried out in a humidity chamber in the absence of liquid water, and an analytical balance is used to measure the weight of the particles. The amount of water vapor that can be absorbed by a porous particle 1 or a treated porous particle 5 disclosed herein depends on the type of particle. For example, silica gel particles are typically reported to absorb about 40 percent of their weight in water.

In other presently preferred exemplary embodiments, treated porous particles have a water vapor uptake at 30° C. and 80% relative humidity that is at least 50, 55, 60, 65, 70, 75, or 80 percent of the moisture vapor uptake of a comparative plurality of particles comprising no hydrophobic groups. In some exemplary embodiments, the interior surfaces of the treated porous particles are said to be "substantially untreated" when they have a water vapor uptake at 30° C. and 80% relative humidity that is at least 60, 65, 70, 75, or 80 percent of the moisture vapor uptake of a comparative plurality of particles comprising no hydrophobic groups. A comparative plurality of particles comprising no hydrophobic groups refers to a plurality of particles that is the same as the plurality of treated particles except having no hydrophobic treatment. For example, the comparative plurality of particles has the same size and pore size distribution as the plurality of treated particles and has the same chemical make-up as the treated porous particles before such particles are treated.

In additional exemplary embodiments of methods of treating the plurality of particles according to the present disclosure, when the treated porous particles are sprinkled on a surface of water to form a single layer, at least 75 percent of the particles float on the surface of the water, and the treated porous particles absorb at least 20 percent of their weight of water vapor after 24 hours at 30° C. and 50 percent relative humidity. In some such embodiments, one gram of the treated porous particles is sprinkled on 10 milliliters (mL) of water in a 20-mL vial. In some particular such embodiments, the particles have a water vapor uptake at 30° C. and 80% relative humidity that is at least 60% of the water vapor uptake of a comparative plurality of particles that do not comprise the hydrophobic groups. In some such embodiments, when at least a portion of the plurality of particles is exposed to aqueous liquid, the plurality of particles decreases relative humidity to a greater extent than a comparative plurality of particles that do not comprise the hydrophobic groups.

Treated porous particles 5 according to present disclosure include treated silica gel particles, treated montmorillonite clay particles, treated molecular sieves and treated activated carbon. The treated porous particle may have an average particle size in a range from 0.075 millimeter (mm) to 10 mm (e.g., from 0.1 mm to 10 mm, 0.5 mm to 5 mm, or 0.5 mm to 1 mm). The median pore size may vary as long as the pores are large enough to allow access to water molecules. In some exemplary embodiments, the interior pores have a median pore size in a range from 1 nanometers (nm) to 10 nm (e.g., 2 nm to 3 nm, 2 nm to 7 nm, 4 nm to 7 nm, 8 nm to 10 nm, or 4 nm to 10 nm). In some exemplary embodiments, the treated porous particles have a bimodal porous structure wherein the pores have two different median sizes selected from any of the listed ranges.

The porous particles 1 before treatment can be obtained from a variety of commercial sources (e.g., AGM Container Controls, Inc., Tucson, Ariz.; International Silica Gel Co., LTD, Shandong, China; and SIGMA-ALDRICH, St. Louis, Mo.). In some exemplary embodiments, the treated porous particles may comprise a color-change indicator (e.g., cobalt chloride) to show color change upon absorption of moisture.

Figure 2:
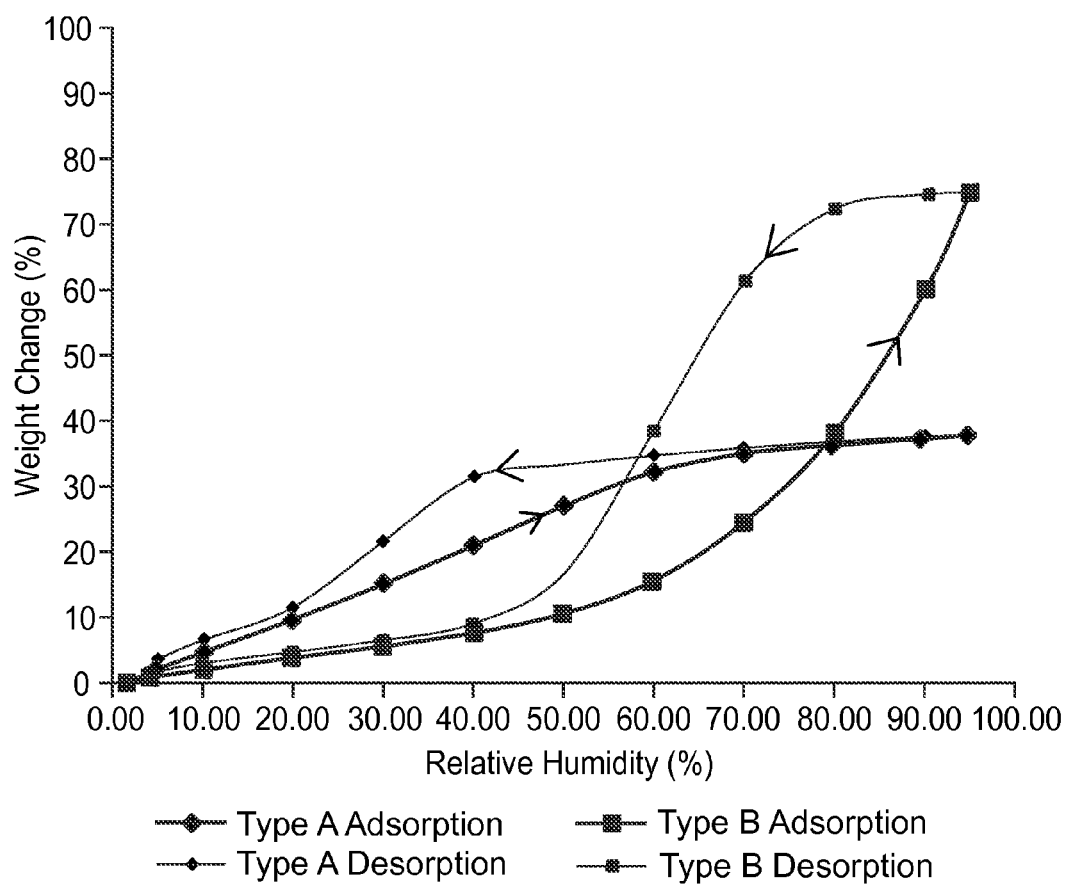
FIG. 2 shows graphical representations of exemplary water vapor adsorption and desorption isotherms for exemplary treated porous particles treated according to some illustrative embodiments of the present disclosure.

Depending on the pore size distribution and internal pore structure, silica gel desiccants useful as porous particles in practicing the processes of the present disclosure may show differences in the adsorption/desorption of water vapor as a function of the relative humidity. FIG. 2 shows graphical representations of exemplary water vapor adsorption and desorption isotherms for exemplary hydrophobic surface-treated porous particles treated according to some illustrative embodiments of the present disclosure. Vapor phase treated hydrophobic silica gel particles having a narrow pore size distribution (e.g. Type-A; mean pore diameter of 2-3 nm; available from International Silica Gel, China) exhibit the water vapor adsorption (bold plot line; large diamonds) and desorption (thin plot line; small diamonds) isotherms as shown in FIG. 2. Vapor phase treated hydrophobic silica gel particles having a wider pore size distribution (e.g. Type-B; mean pore diameter of 4-7 nm; available from International Silica Gel, China) exhibit the measured water vapor adsorption (bold plot line; large squares) and desorption (thin plot line; small squares) isotherms as shown in FIG. 2. The adsorption/desorption isotherms of the two types of silica gel desiccants were measured at 25° C.

The water adsorption indicates that Type-A silica gel has a narrow pore size distribution, since the adsorption occurs at lower vapor pressure compared to Type-B silica gel. As the pore size distribution becomes wider, water adsorbs at higher relative humidity. It is also known that water adsorbed in the narrow pores has solid ice-like structure, while it adsorbs in wider pores as a liquid phase.

Although the hydrophobic treatment of silica gel particles is known, in general, this hydrophobic treatment is designed to make both the external surface and the internal pore surfaces hydrophobic. Partially-treated particles that may be obtained from methods to treat both the external surfaces and internal pore surfaces hydrophobic may not float in water if the external surface was not covered with a sufficient amount of hydrophobic groups or if the hydrophobic group hydrolyzes upon contact with water. Also, such partially-treated particles may not absorb, for example, at least 20 percent of their weight in water if the majority of the external and interior surfaces were made hydrophobic.

Typically, previously known solvent and vapor techniques for the hydrophobic treatment of silica gel particles do not readily allow stopping the reaction at a point where the interior pore surfaces are not treated. Also, radio-frequency carbon tetrafluoride plasma as a sole treating agent treats interior pore surfaces and external surfaces of silica gel; see e.g., K. Furukawa et al., *Journal of Materials Science Letters*, 19, 1545-1547 (2000).

In contrast, the treated porous particles according to and/or prepared according to the present disclosure comprise hydrophilic interior pore surfaces, which allows the treated particles to be useful, for example, as desiccants. Hydrophobic silica gel in which both the external surface and the internal pore surfaces are hydrophobic would not be useful as desiccants. In some exemplary embodiments, a plurality of treated porous particles comprise less than 25 (in some exemplary embodiments, less than 20, 15, 10, 5, 4, 3, 2, or 1) percent of particles wherein the external surface and the interior pore surfaces are both treated with hydrophobic groups. This plurality of treated porous particles can be referred to as substantially free of particles wherein the external surface and the interior pore surfaces are both treated with hydrophobic groups.

Methods of Making Treated Porous Particles

In one aspect, the disclosure describes a method of treating a plurality of porous particles. The method comprises providing a plurality of porous particles, each porous particle having an external surface and a plurality of pores with interior pore surfaces, and treating the external surfaces of the porous particles by contacting the external surfaces with a hydrophobic agent while causing the interior pore surfaces to remain substantially free of the hydrophobic agent. In some exemplary embodiments, treating the external surface of the porous particle comprises forming a layer comprising silicon, hydrogen, and carbon on at least a portion of the external surface of the porous particle by plasma deposition. In certain such embodiments, the method further comprises forming a layer comprising fluorine and carbon by plasma deposition on at least the portion of the layer comprising silicon, hydrocarbon, and carbon.

The methods of treating a porous particle 5 according to any of the embodiments described herein comprise treating an external surface of a porous particle 1 with a hydrophobic agent while allowing interior pore surfaces of the porous particle to remain substantially untreated. "Substantially untreated" has the same meaning described above. In some exemplary embodiments, only the external surface of the porous particle 1 is treated with the hydrophobic agent. Suitable treatment processes are described below.

Treatment Process 1

Methods of plasma treatment of porous materials are provided in U.S. Pat. No. 6,878,419 (David et al.). Also, methods and apparatuses for plasma treatment of particles are provided in U.S. Pat. No. 6,015,597 (David) and U.S. Pat. No. 6,197,120 (David). In some exemplary embodiments, the method of making a treated porous particle comprises forming a layer comprising silicon, hydrogen, and carbon on at least portion of the external surface of the porous particle by plasma deposition. Forming this layer may be carried out by ionizing a gas comprising an organosilicon compound selected from the group consisting of an alkylsilane, an alkoxysilane, an alkylenepolysilane, an alkylpolysilane, an alkenyl silane, an aryl silane, and combinations thereof.

Exemplary alkylsilanes include tetramethylsilane, methylsilane, dimethylsilane, diethylsilane, diethylmethylsilane, propylsilane, trimethylsilane, and ethylsilane. Exemplary alkoxysilanes and siloxanes include tetraethylorthosilicate (TEOS), and tetramethylcyclotetrasiloxane (TMCTS). Exemplary alkylenepolysilanes include disilanomethane, bis (methylsilano)methane, 1,2-disilanoethane, 1,2-bis(methylsilano)ethane, 2,2-disilanopropane, dimethyldisilanoethane, dimethyldisilanopropane, tetramethyldisilanoethane, and tetramethyldisilanopropane. Exemplary alkenylsilanes include vinylmethylsilane and divinyldimethylsilane. Exemplary aryl silanes include phenylsilane, phenyldimethylsilane, and phenyltrimethylsilane. Exemplary alkylpolysilanes include 1,1,2,2-tetramethyldisilane, hexamethyldisilane, 1,1,2,2,3,3-hexamethyltrisilane, and 1,1,2,3,3-pentamethyltrisilane.

The organosilicon compound may have substituents such as amino groups, hydroxyl groups, and/or halo (e.g., fluoro, bromo, chloro) groups, although typically they are unsubstituted. In some exemplary embodiments, the organosilicon compound has at least one C—H bond, which may be an sp3, sp2 or sp C—H bond. Typically, the organosilicon has a plurality of C—H bonds, for example, at least 2, at least 3, at least 5, at least 9, and/or even at least 12 C—H bonds, or more. Typically useful organosilicon compounds have sufficient vapor pressure under plasma treatment conditions that a plasma is formed.

In some exemplary embodiments of methods of making a treated porous particle, the method further comprises treating at least a portion of the layer comprising silicon, hydrogen, and carbon with a fluorinated compound (e.g., by plasma treatment or deposition). The fluorinated compound is typically a hydrocarbon in which at least some of the hydrogen atoms are replaced by fluorine atoms. The fluorinated compound may be straight-chained, branched, or cyclic, and may be fully saturated or partially unsaturated. The fluorinated compound typically contains up to 5 carbon atoms (e.g., up to 4, 3, or 2). For plasma deposition, the fluorinated compound typically contains at least 2 or 3 carbon atoms. In some exemplary embodiments, the fluorinated compound is perfluorinated (i.e., all C—H bonds are replaced by C—F bonds). In some exemplary embodiments, the fluorinated compound is selected from the group consisting of perfluoropropane, carbon tetrafluoride, trifluoromethane, difluoromethane, pentafluoroethane, perfluoropropene, perfluorobutane, and perfluorobutene and combinations thereof.

In certain exemplary embodiments, plasma treatment is done in two steps. For example, when the method of making a treated porous particle comprises forming a layer comprising silicon, hydrogen, and carbon on at least portion of the external surface of the porous particle by plasma deposition and treating at least a portion of the layer comprising silicon, hydrogen, and carbon with a fluorinated compound by plasma deposition, a first plasma treatment typically includes treating the porous particle 1 under vacuum with a gas (e.g., an organosilicon compound as described above) and igniting the plasma.

Without intending to be bound by theory, it is believed that when the gas is, for example, tetramethylsilane (TMS), the external surface of the treated porous particle is covered with a layer comprising methyl groups, which provide a hydrophobic external surface. A second plasma treatment, when used, typically includes treating the treated porous particle 5 under vacuum with a second gas (e.g., a fluorinated compound as described above) and igniting the plasma.

Without intending to be bound by theory, it is believed that the second step will replace some of the active hydrogen (e.g., C—H bonds) on the surface of the porous particle with fluorine to produce CF, $CF_2$, or $CF_3$ groups on the surface. If a depositing fluorochemical plasma is used (e.g., with fluorochemicals having at least 2 or 3 carbon atoms), it is believed that a layer comprising fluorocarbon species is formed on the surface. Each of the two treatment steps may be carried out, for example, for a total of at least 5, 10, 20, 30, 45, or 60 minutes each or longer. Typically, the plasma treatments are carried out at pressures of up to about 1000, 750, 500, 250, 100, or 75 mTorr (133, 100, 67, 33, 13, or 10 Pa).

Plasma treatments generally require mixing of the porous particles 1 to maximize the amount of the external surface area that is exposed to the plasma. When plasma treatments are carried out on a laboratory scale, the mixing can be carried out by hand. For example, in the two-step process described above each step may be interrupted a number of times (e.g., 2, 3, or 4) to stir the porous particles. The gas is then reintroduced and the plasma reignited. In larger scale treatments, the mixing may be carried out, for example, with a mixing paddle that may continuously rotate during the process.

Methods of making a treated porous particle according to the present disclosure using plasma typically also include providing a reaction chamber having a capacitavely-coupled system comprising at least one grounded electrode and at least one electrode powered by a radio frequency source; generating a plasma comprising reactive species in the chamber causing an ion sheath to form around at least one of the electrodes; and locating a plurality of porous particles in the ion sheath. In some exemplary embodiments, the method further comprises agitating the plurality of porous particles in a manner to expose their external surfaces to the reactive species in the plasma.

In the plasma treatments described above, the plasma (e.g., the silane plasma or the fluorine plasma) may include other gaseous component(s), for example, nitrogen or ammonia, as long as the gaseous components don't prevent the external surface from becoming hydrophobic. Thus, the term "gas," in embodiments wherein a gas is used, refers to a single compound or a mixture of two or more compounds.

Plasma treatment may provide a treated porous particle with a unique structure because it typically treats only the external surface of the particle. Typically, for the treated porous particles disclosed herein, the pore size is in the range of up to tens of nanometers while the mean free path of the reactive species in the plasma (i.e., the average distance traveled by a species before it collides with another species) is not smaller than 20 microns. Also, plasma deposition methods can form layers of hydrophobic species on a surface. The method described in any of the above embodiments may provide a treated silica gel particle comprising an external surface and interior pore surfaces, wherein the external surface has up to 5 (e.g, 4, 3, 2.5, 2, or 1) atomic percent silicon atoms up to a depth of 50 angstroms, as determined by x-ray photoelectron spectroscopy.

In some of these embodiments, the external surface is free of silicon atoms. In some exemplary embodiments, the treated porous particle prepared by plasma treatment has at least 10, 20, 30, or 40 atomic percent fluorine on the outer 50 angstroms of its external surface, as determined by x-ray photoelectron spectroscopy. In some exemplary embodiments, the treated porous particle prepared by plasma treatment has less than 20, 15, 10, or 5 atomic percent oxygen on the outer 50 angstroms of its external surface, as determined by x-ray photoelectron spectroscopy. In any of these embodiments, the interior pore surfaces a typically at least partially hydrophilic.

In some exemplary embodiments, the method of making a treated porous particle 5 according to any of the aforementioned embodiments of treated porous particles comprises exposing the porous particle 1 to at least one of water vapor, methanol vapor, or ethanol vapor, and subsequently exposing the porous particle to a second vapor comprising a reactive organosilane compound. This method is hereinafter called "the second method." Treating silica surfaces with reactive organosilane compounds is known, for example, in the semiconductor and in printing industries.

In semiconductor industry silicon wafers are treated with dichlorodimethylsilane vapor. In printer toner cartridges, silica gel particles treated with dichlorodimethylsilane on both the interior pore surfaces and the external surfaces are used as lubricants. It has been shown in the evaluation of nonporous silica particles that the reaction between dichlorodimethylsilane and the silica surface is enhanced by the presence of surface water.

However, in some exemplary embodiments of the methods disclosed herein, the reaction between vapor phase reactive organosilane compounds and a porous particle 1 has been unexpectedly found to preferentially incorporate hydrophobic groups on the external surface of the porous particle without affecting the desiccant capacity of the interior pore surfaces of the particle.

Treatment Process 2

In process 2, exposing the porous particles to at least one of water vapor, methanol vapor, or ethanol vapor takes place before exposing the porous particles to the second vapor comprising the reactive organosilane compound. In certain such embodiments of Process 2, at least a portion of the water vapor, methanol vapor, or ethanol vapor condenses within at least a portion of the plurality of pores of the porous particles, thereby at least partially occluding the interior pore surfaces, before exposing the porous particles to the second vapor comprising the reactive organosilane compound. In additional such embodiments, the method further comprises substantially removing the condensed water vapor, methanol vapor, or ethanol vapor from the pores after exposing the porous particles to the second vapor comprising the reactive organosilane compound, optionally wherein substantially removing the condensed water vapor, methanol vapor, or ethanol vapor from the pores is accomplished by heating the particles, exposing the particles to a vacuum, or a combination thereof.

In an additional exemplary process (Process 2) for treating porous particles according to the present disclosure, treating the external surfaces of the porous particle comprises exposing the porous particles to at least one of water vapor, methanol vapor, or ethanol vapor, and exposing the porous particles to a second vapor comprising a reactive organosilane compound which reacts to form the hydrophobic agent. In some exemplary embodiments, exposing the porous particles to at least one of water vapor, methanol vapor, or ethanol vapor takes place before exposing the porous particles to the second vapor comprising the reactive organosilane compound.

In certain such embodiments of Process 2, at least a portion of the water vapor, methanol vapor, or ethanol vapor condenses within at least a portion of the plurality of pores of the porous particles, thereby at least partially occluding the interior pore surfaces, before exposing the porous particles to the second vapor comprising the reactive organosilane compound. In additional such embodiments, the method further comprises substantially removing the condensed water vapor, methanol vapor, or ethanol vapor from the pores after exposing the porous particles to the second vapor comprising the reactive organosilane compound, optionally wherein substantially removing the condensed water vapor, methanol vapor, or ethanol vapor from the pores is accomplished by heating the particles, exposing the particles to a vacuum, or a combination thereof.

In a first step of Process 2 for treating porous particle 5, porous particles 1 are first exposed to at least one of water vapor, methanol vapor, or ethanol vapor. This exposure can be carried out at ambient pressure (e.g., in a humidity chamber at, for example, 50 to 95 percent relative humidity) or under reduced pressure (e.g., using apparatus 300 shown in FIG. 3A or 3B) and at ambient temperature or elevated temperature (e.g., in a range from 25° C. to 40° C. or 25° C. to 35° C.).

In a second step of Process 2 for treating porous particle 5, porous particles 1 are exposed to a second vapor comprising a reactive organosilane compound. This exposure is typically carried out under reduced pressure (e.g., in a range from 0.5 torr to 150 torr (67 Pa to 2×10$^4$ Pa) and may be carried out at ambient temperature or elevated temperature (e.g., in a range from 25° C. to 40° C. or 25° C. to 35° C.). In some exemplary embodiments, the vapor comprising the reactive organosilane compound is at a pressure of at least 400 Pa, 650 Pa, 1000 Pa, 1300 Pa, or at least 10000 Pa when it comes into contact with the particles. It has been unexpectedly found that the performance of the particles as desiccants (e.g., when exposed to aqueous liquids) was improved when the vapor comprising the reactive organosilane compound was at a pressure of at least 1000 Pa (e.g., about 1300 Pa).

Without intending to be bound by theory, it is believed that a pressure of at least 1000 Pa minimizes the diffusion of the reaction organosilane compound into the pores of the particle so that the treatment remains on the external surface. Conveniently, a process pressure of 10 torr (1300 Pa) can be used when the vapor pressure of the reactive organosilane compound is above 10 torr (1300 Pa); typically the water vapor, methanol vapor, or ethanol vapor inside the pores of the particles is not pumped out at this pressure.

In either the first step or the second step described above, the method may further comprise agitating a plurality of porous particles in a manner to expose their external surfaces to the water vapor, methanol vapor, ethanol vapor, or the second vapor.

Figure 3A:
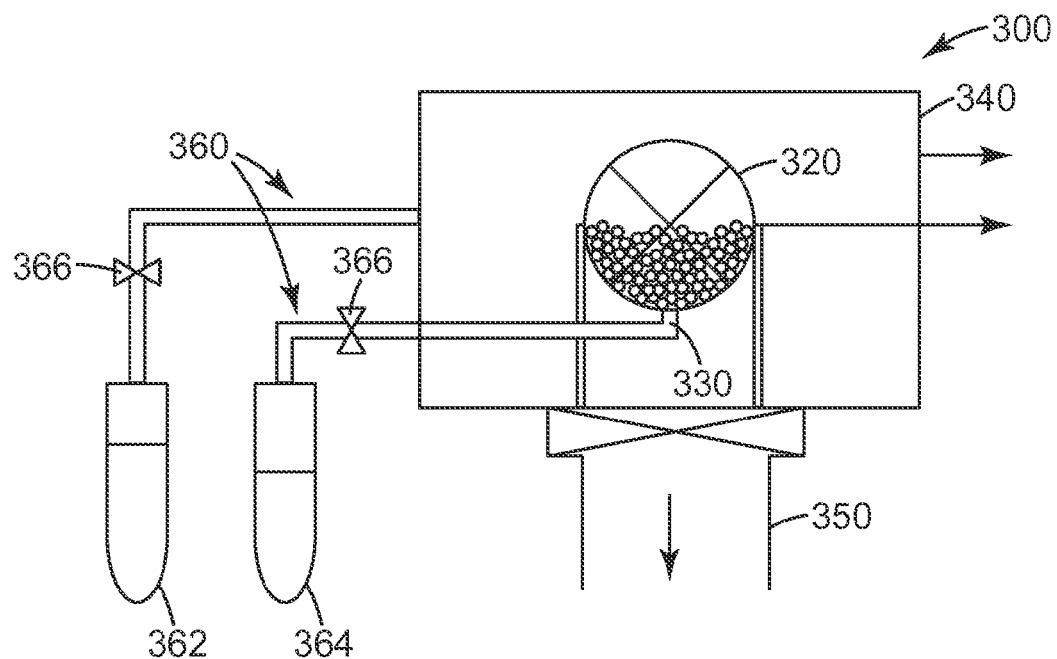
FIG. 3A is a schematic side view of an exemplary apparatus used to treat porous particles with a first and second vapor phase in an illustrative method of making treated porous particles according to some illustrative embodiments of the present disclosure.

In practicing the second exemplary method of treating porous particles (Process 2), the first and second steps can be advantageously carried out, for example, using apparatus 300 shown in FIG. 3A. As shown in FIG. 3A, two liquid holder assemblies 360, one for the reactive organosilane compound and one for water, methanol or ethanol; can be used to deliver vapor to vacuum chamber 340 connected to vacuum pump 350. The vacuum chamber is typically a hollow cylinder capable of being evacuated to a background pressure of up to 10$^{-6}$ torr (10$^{-4}$ Pa).

Each liquid holder assembly can contain a vacuum compatible glass tube 362, 364 sealed off at one end and an attached valve 366 to control the on/off of the vapor source. If the exposure to water vapor, methanol vapor, or ethanol vapor is carried out, for example, in a humidity chamber as described above, one of the two liquid holder assemblies, which includes tube 362, need not be used. Inside the vacuum chamber 340 is a particle agitator 320 that has an inlet port 330 for the vapor. The second vapor comprising the reactive organosilane compound can be metered into the chamber 340, for example, using a mass flow controllers or needle valves. The mass of reactive organosilane consumed can be monitored using conventional techniques.

Figure 3B:
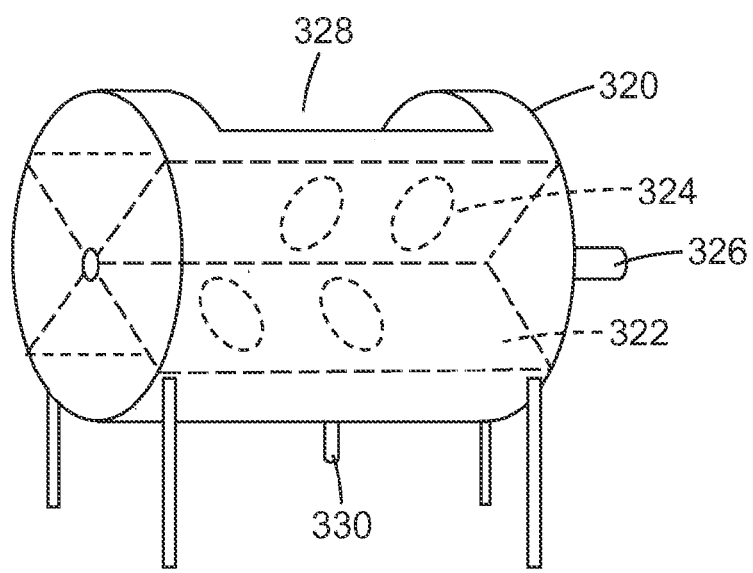
FIG. 3B is a schematic perspective view of an exemplary particle agitator portion of the apparatus in FIGS. 3A and 3C.

A representative particle agitator 320 is shown in more detail in FIG. 3B. Particle agitator 320 is a hollow cylinder with a rectangular opening 328. Agitator 320 is fitted with a shaft 326 aligned with its axis, to which is bolted four rectangular blades 322, which form an agitation mechanism or paddle wheel for the particles in the agitator 320. The blades 322 each contain two holes 44 to promote communication between the particle volumes contained in each of the four quadrants formed by the blades 322 and the agitator cylinder 320. Modes of use of this apparatus 300 are described below in the examples.

FIGS. 4A through 4D schematically illustrate different embodiments of the second method (Process 2) of making the treated porous particles disclosed herein, where the exposure to at least one of water vapor, methanol vapor, or ethanol vapor is carried out for different lengths of time. Particles 420 may be dried using conventional drying techniques before the exposure to at least one of water vapor, methanol vapor, or ethanol vapor. Particles 401 in the embodiments illustrated in FIGS. 4A to 4D have different amounts of absorbed surface water and different amounts of surface hydroxyl groups resulting from the exposure to at least one of water vapor, methanol vapor, or ethanol vapor for different lengths of time.

Figure 4A:
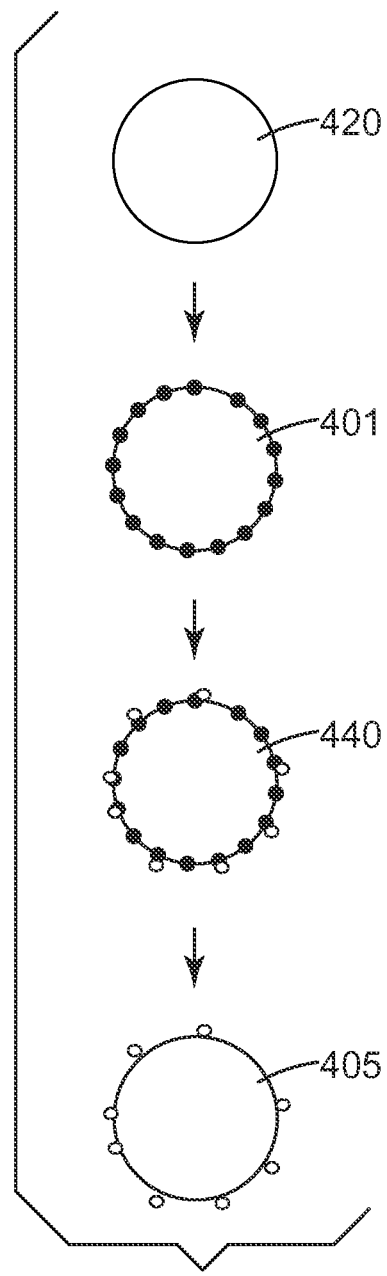
Figure 4B:
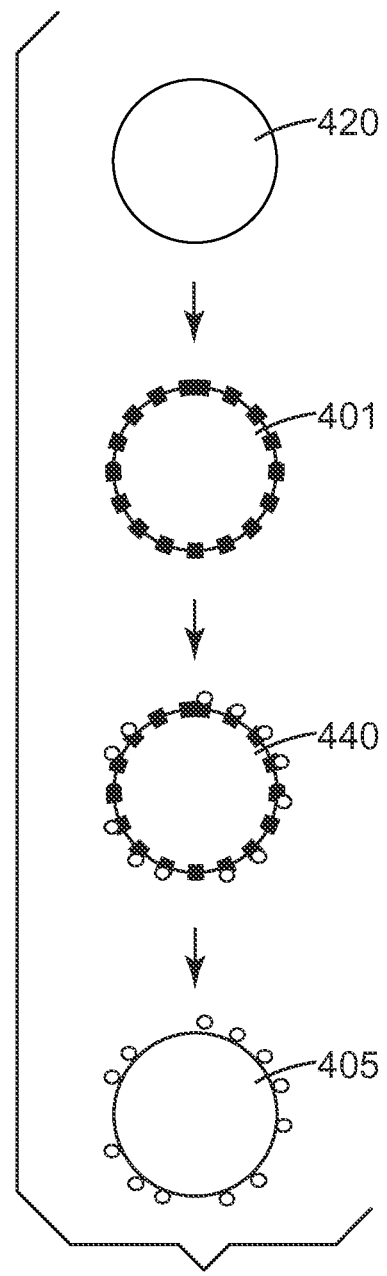

FIG. 4D illustrates the longest exposure time to at least one of water vapor, methanol vapor, or ethanol vapor, and FIG. 4A illustrates the shortest exposure time, with FIGS. 4B and 4C illustrating intermediate exposure times. Particles 440 in the embodiments illustrated in FIGS. 4A to 4D result from exposure to the reactive organosilane compound, which reacts in the areas where the surface water and/or surface silanols are present in particles 401. Treated porous particles 405 illustrated in FIGS. 4A to 4D have been dried to remove remaining absorbed surface water. Depending on the length of the exposure of the particles 401 to the water vapor, methanol vapor, or ethanol vapor, the treated porous particles 405 may have different levels of coverage.

While non-uniform treatments may result from short exposure times to water vapor, methanol vapor, ethanol vapor, and the organosilane, longer exposure times may result in more uniform coverage of hydrophobic groups and better, more consistent performance of the particles and desiccants (e.g., when exposed to liquid water). In some exemplary embodiments, exposing the porous particles to the water vapor, methanol vapor, ethanol vapor, and reactive organosilane is carried out for at least 15, 20, 25, or 30 minutes up to about 1, 2, or 3 hours. The time of exposure to the reactive organosilane compound also can affect the amount of hydrophobic groups on the surface.

Treatment Process 3

Although Process 2 substantially improves the selective treatment of the external surfaces of the porous particles relative to their interior pore surfaces, for some applications (e.g. where it is desirable for the particles to repel aqueous fluids yet adsorb water vapor, for example, in catamenial receptors), it may be desirable to make the entire exterior particle surfaces hydrophobic while substantially maintaining the hydrophilic character of the interior pore surfaces. One way to achieve this is to pre-react or pre-polymerize the organosilane in the vapor phase before the vapor reaches the porous particles. By pre-polymerizing the organosilane in the vapor phase to form dimers, trimers, and higher oligomers, the resulting dimers, trimers, and higher oligomers will reach a molecular size sufficient to exclude the pre-polymerized organosilane from penetrating into the pores of the porous particles.

However, because the dimer, trimer and higher oligomers of DDMS have a lower vapor pressure at ambient conditions and will tend to condense on the internal surfaces of the vacuum chamber, it may be necessary to increase the treatment time significantly, or otherwise optimize the treatment conditions (e.g. temperature, pressure, organosilane and water, methanol, or ethanol vapor pressures, and the like.

Thus, in an additional exemplary process (Process 3) for treating porous particles according to the present disclosure, treating the external surfaces of the porous particle comprises treating an external surface of a porous particle with a hydrophobic agent while causing interior pore surfaces of the porous particle to remain substantially untreated. In some exemplary embodiments, only the external surface of the porous particle is treated with the hydrophobic agent.

Figure 3C:
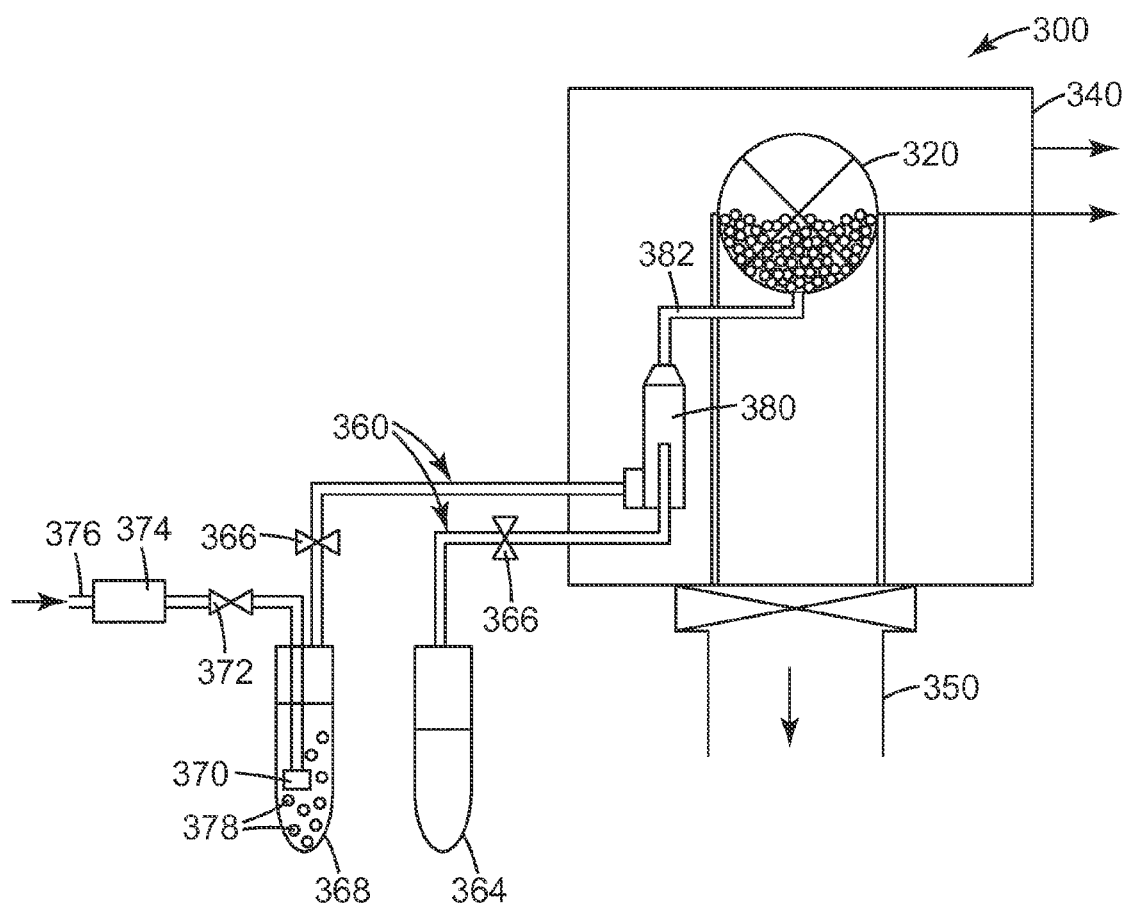
FIG. 3C is a schematic side view of another exemplary apparatus used to treat porous particles with a first and second vapor phase in another illustrative method of making treated porous particles according to some embodiments of the present disclosure.

In some exemplary embodiments of Process 3 for treating the external surfaces of the porous particle 5, an alternative method of delivering the organosilane vapor to the vacuum chamber and the surface of the particles to be surface-treated, may be advantageously employed. A schematic of one exemplary apparatus 300 for carrying out Process 3 is shown schematically in FIG. 3C. As shown in FIG. 3C, two liquid holder assemblies 360, one for the reactive organosilane compound and one for water, methanol, or ethanol can be used to deliver vapor to vacuum chamber 340. Vacuum chamber 340 is connected to a vacuum pump 350 capable of evacuating the vacuum chamber 340 to a background pressure of about $10^{-6}$ torr ($10^{-4}$ Pa) or lower. Inside the vacuum chamber 340 is a particle agitator 320 (which may be as generally shown in FIG. 3B) that has a single inlet port 382 for the combined first and second vapor stream.

As shown in FIG. 3C, one liquid holder assembly can contain a vacuum compatible glass tube 364 sealed off at one end and an attached valve 366 to turn on or off the first vapor source comprising the reactive organosilane compound. The second vapor source can be formed by passing an inert gas (e.g., nitrogen) from a source 376 through a flowrate metering means (e.g., a mass flow controllers 374 and/or needle valves 372) and into a gas dispersion tube 370 immersed in a gas bubbler 368 containing liquid water, methanol, or ethanol, thereby forming bubbles 378 of the inert gas in equilibrium with water, methanol, or ethanol vapor.

The inert gas containing the water, methanol, or ethanol vapor passes into an annular mixing nozzle 380, where it mixes with the organosilane compound before passing into the chamber 340 through outlet tube 382, which connects to the inlet tube 330 (see FIG. 3B) of the particle agitator 320. Attached valves 366 may be used to turn on or off the first and second vapor sources. The mass of reactive organosilane consumed can be monitored using conventional mass balance techniques.

In this method of treating porous particles, which is presently preferred for porous particles having a wide pore size distribution, or when it is desirable to treat substantially all of the exterior surface of the porous particles while leaving the interior pore surfaces substantially untreated, the process parameters are similar to those used in Process 2. However, Process 3 is intended to deliver a pre-mixed mixture of the organosilane with the water, methanol, or ethanol vapor to the vacuum chamber. Pre-mixing causes the organosilane to undergo polymerization before depositing as a coating on the particles.

By passing a known flow rate of nitrogen through the water/methanol bubbler 368 to produce a pre-determined amount at least one of water vapor, methanol vapor, or ethanol vapor or methanol vapor at the annular mixing nozzle 380, it is possible to rapidly polymerize the organosilane monomer to form a higher molecular weight oligomer. By controlling the amount of water, methanol, or ethanol vapor at the annular mixing nozzle 380, desired dimer, trimer or higher oligomer formation can be achieved before the reaction product deposits on the particulates.

In certain exemplary embodiments of any of the foregoing processes, the method of treating the surfaces of porous particles further comprises exposing the porous particles to a third vapor comprising a volatile compound non-reactive with the reactive organosilane before exposing the porous particles to the at least one of water vapor, methanol vapor, or ethanol vapor and the second vapor, wherein at least a portion of the volatile compound condenses within at least a portion of the plurality of pores of the porous particles, thereby at least partially occluding the interior pore surfaces.

In some such exemplary embodiments, the volatile compound is selected from the group consisting of molecular nitrogen, carbon dioxide, a $C_1$-$C_2$ hydrocarbon, and combinations thereof. In certain such exemplary embodiments, the method further comprises substantially removing the condensed volatile compound from the pores after exposing the porous particles to the second vapor comprising the reactive organosilane compound, optionally wherein substantially removing the condensed volatile organic compound from the pores is accomplished by heating the particles, exposing the particles to a vacuum, or a combination thereof.

In certain of the foregoing embodiments which comprise treating the external surfaces of the porous particle by exposing the porous particles to at least one of water vapor, methanol vapor, or ethanol vapor, at least a portion of the at least one of water vapor, methanol vapor, or ethanol vapor reacts with at least a portion of the reactive organosilane compound in a vapor phase outside of the pores of the porous particles.

In some particular examples of such embodiments which comprise treating the external surfaces of the porous particle by exposing the porous particles to at least one of water vapor, methanol vapor, or ethanol vapor, the reactive organosilane compound comprises at least two silane functional reactive groups. In further examples of such embodiments, the reactive organosilane compound is selected from dichlorodimethylsilane and dichlorodiethylsilane. In additional examples of such embodiments, the reactive organosilane compound has a vapor pressure at 25° C. of from 133 Pa to 26,600 Pa. In certain presently preferred embodiments, treating the external surface of the porous particle takes place at a total vapor pressure of from 1,330 to 26,600 Pa.

In other examples of any of the foregoing processes, the plurality of pores exhibit a median pore size of at least 1 nm and no more than 4 nm, and exposing the porous particle to the second vapor comprising the reactive organosilane compound occurs at a total vapor pressure of from 1,330 to 19,950 Pa. In other presently preferred embodiments, the plurality of pores exhibits a median pore size of at least 4 nm and no more than 10 nanometers, and exposing the porous particle to the second vapor comprising the reactive organosilane compound occurs at a total vapor pressure of from 6,650 to 26,600 Pa. The latter pressure range is presently particularly preferred when Process 2 is used to treat porous particles having a wide pore size distribution.

In any of the foregoing process, the porous particles are preferably selected from the group consisting of porous inorganic particles, porous organic particles, porous metal particles, porous (co)polymeric particles, porous carbon particles, porous clay particles, porous molecular sieve particles, porous zeolite particles, porous desiccant particles, and combinations thereof.

In some such embodiments, the treated porous particle is a treated silica gel particle, a treated montmorillonite clay particle, a treated molecular sieve, or a treated activated carbon particle. In some particular exemplary embodiments, the hydrophobic groups comprise siloxanes having alkyl groups, aryl groups, or combinations thereof. In some exemplary embodiments, the treated porous particle is a silica gel particle with an external surface having up to 5 atomic percent silicon atoms up to a depth of 50 angstroms, as determined by x-ray photoelectron spectroscopy.

In some exemplary embodiments, the plurality of particles further comprises untreated desiccant particles (e.g., silica gel, montmorillonite clay, molecular sieves, or activated carbon). In some particular exemplary embodiments, the plurality of particles is substantially free of particles wherein the external surface and the interior pore surfaces are both treated with hydrophobic groups. In certain exemplary embodiments, the plurality of particles further comprises absorbent particles or fibers comprising at least one of superabsorbent polymers, hydrophilic nonwovens, or wood pulp.

In any of the foregoing aspect and embodiments, at least a portion of the external surface of the treated porous particle comprises hydrophobic groups, the hydrophobic groups preferably comprising at least one of alkyl or aryl groups, further wherein the alkyl and aryl groups are each optionally substituted with fluorine, and additionally wherein the interior pore surfaces are at least partially hydrophilic. In some such embodiments, the hydrophobic groups comprise siloxanes having alkyl groups, aryl groups, or combinations thereof.

In some exemplary presently preferred embodiments of any of the foregoing processes, the reactive organosilane compound is represented by formula $R_xSiY_{4-x}$, wherein each Y is independently a hydrolysable group, which may be selected from the group consisting of halogen (i.e., —F, —Cl, —Br, or —I), alkoxy (e.g., having 1 to 6, 1 to 4, or 1 to 2 carbon atoms), aryloxy (e.g., phenoxy), or acyloxy (e.g., having 1 to 6, 1 to 4, or 1 to 2 carbon atoms), each R is independently alkyl, alkenyl, aryl, arylalkylenyl, or alkylarylenyl, each of which may optionally be substituted (e.g., with cyano or halogen), and x is 1, 2, or 3. In some exemplary embodiments Y is halogen or alkoxy. Typically, Y is chloro. In some exemplary embodiments, each R is alkyl (e.g., methyl, ethyl, n-propyl, isopropyl, n-butyl, isobutyl, tert-butyl, n-pentyl, isopentyl, neopentyl, tert-pentyl, n-hexyl, n-heptyl, n-octyl, isooctyl, 2,2,4-trimethylpentyl, n-nonyl, n-decyl, n-dodecyl, n-octadecyl cyclopentyl, cyclohexyl, cycloheptyl, or methyl-cyclohexyl).

In some exemplary embodiments, each R is independently methyl, ethyl, or phenyl. In some exemplary embodiments, each R is methyl. Exemplary alkenyl groups include vinyl, allyl, and 5-hexene-1-yl. Exemplary aryl groups include phenyl, naphthyl, anthryl, and phenanthryl. Exemplary alkylarylenyl groups include o-, m-, p-tolyl, xylyl and ethylphenyl, and exemplary arylalkylenyl groups include benzyl and alpha- and beta-phenylethyl. Exemplary fluoroalkyl groups include 3,3,3-trifluoro-n-propyl, 2,2,2,2',2',2'-hexafluoroisopropyl, 8-heptafluoroisopropyl. Many reactive organosilane compounds represented by formula $R_xSiY_{4-x}$ are commercially available (e.g., from Huls America, Inc., Cincinnati, Ohio, and Sigma-Aldrich Corp., St. Louis, Mo.); other organosilane compounds represented by formula $R_xSiY_{4-x}$ can be prepared according to known methods. In some exemplary embodiments, the reactive organosilane compound is selected from the group consisting of dichlorodimethylsilane, trichloromethylsilane, chlorotrimethylsilane, and combinations thereof.

Without intending to be bound by theory it is believed that the reactive organosilane compound represented by formula $R_xSiY_{4-x}$ will first undergo hydrolysis with pre-adsorbed surface water to form a silanol. The silanols can undergo condensation reactions with the surface —SiOH groups and/or other molecules of the reactive organosilane compound to make short polysiloxane units. Polysiloxanes with terminal —SiOH groups can also react with surface silanol groups through condensation reactions. The R groups from the organosilane compound represented by formula $R_xSiY_{4-x}$ on the resulting siloxanes and polysiloxanes render the surface of the treated porous particles hydrophobic.

The treated porous particles according to and/or useful for practicing the present disclosure have external surfaces that are at least partially hydrophobic. Typically the treated porous particles absorb liquid water (and other aqueous liquids) at a much lower rate or to a much lower extent than comparable untreated porous particles. Thus, the hydrophobic groups on the external surface help repel aqueous liquids. The internal pore surfaces, being substantially hydrophilic, absorb water vapor.

In a further aspect, the present disclosure describes treated porous particles having hydrophobic groups on the external surface and a hydrophilic interior and methods of making them. The treated porous particles may be useful, for example, as desiccants for controlling humidity within the environment of an absorbent article. Absorbent articles (e.g., sanitary pads and diapers) typically contain superabsorbent polymers (SAP) and/or wood pulp in the core region to absorb and retain fluid. Treated particles disclosed herein in the presence of SAP or wood pulp are shown to decrease the humidity in an environment similar to that adjacent the skin of the user of an absorbent article.

While it is known to incorporate desiccants (e.g., silica gel) into components of absorbent articles to reduce the relative humidity of the environment adjacent the skin of a wearer, when these desiccants are exposed to aqueous liquids, their efficacy is diminished or inconsistent, and they tend to cause a slippery or slimy feeling for the wearer of the absorbent article. It is known to encapsulate desiccants in a pouch made of material that can allow the penetration of moisture vapor and exclude aqueous liquids (e.g., microporous films made with thermally induced phase separation or particle filled membranes). Placing such pouches in the absorbent article may require special process techniques and may therefore be undesirable. The treated porous particles disclosed herein typically repel aqueous liquids and are shown in the present disclosure to reduce the relative humidity near the wearer's skin more consistently and reliably than untreated desiccant particles. They can be added to absorbent articles without the use of pouches or other cumbersome physical isolation techniques.

Exemplary embodiments of surface treatment methods for porous particles are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. All contact angle reported in the Examples are static contact angles reported in degrees. In addition, the following abbreviations and materials are used in the Examples below:
Test Methods
Particle Flotation Test Method (Qualitative)

Deionized water (about 10 mL) was added to a 20-mL glass vial, and an amount of particles sufficient to form a single layer of treated particles was carefully sprinkled on the surface of the water using a spoon spatula. For Examples 1 to 18, Illustrative Examples 1 to 8, and Comparative Example 1, the amount of treated particles was about 1 gram. The treated particles were visually inspected, and an estimate of the percentage of floating treated particles was made. When at least about 75% the treated particles floated on the surface of the water, the treated particles were deemed to pass the floatation test.

When untreated silica gel (obtained from ISG, China) having a particle size from 0.5 mm to 1.0 mm in diameter was subjected to this test, the particles sank to the bottom of the vial typically with a crackling sound. When untreated silica gel (part number: 920014; obtained from AGM Container Controls, Inc., Tucson, Ariz.) having a particle size from 0.5 mm to 1.0 mm in diameter was subjected to this test, the particles sank to the bottom of the vial typically with a crackling sound.

Water Vapor Uptake Test Method

Water vapor absorption was measured for the treated particles, untreated particles, wood pulp particles (Pulp), and super absorbent polymer (SAP) particles. Two grams of sample were weighed into a vial and then placed in a glass jar to expose the particles to 30° C. and 50% and/or 90% relative humidity. The vial was removed from the jar, capped, and weighed. Changes in weight were measured at times indicated in the tables below and recorded.

Liquid Water Uptake Test Method

A porous frit filter was fitted to a conical flask with a side arm. The side arm was connected to house vacuum. The frit was wet with water and vacuum was applied to dry it. Particles (2 grams) were placed on the frit, and 10 mL of deionized water was injected along the walls of the frit glass. The water was allowed to stand for 3 minutes in contact with the particles. After 3 minutes vacuum was pulled through the side arm, and the water that drained into the flask was weighed. The water uptake value was then calculated. The procedure was repeated three times for each type of particle.

Surface Analysis of Treated Particles

Electron Spectroscopy for Chemical Analysis (ESCA) was performed on particles using the following procedure. Triplicate analyses of the surface of the samples were performed using an X-ray photoelectron spectrometer obtained from Kratos Analytical, Chestnut Ridge, N.Y., under the trade designation "AXIS ULTRA", which excites photoelectrons using a monochromatic Al x-ray source. Emitted photoelectrons were detected at a 90° take-off angle with respect to the sample surface. Spectra were obtained from which the surface composition was determined by integrating the major peak areas and applying the appropriate sensitivity factors. ESCA is quantitative and represents a sampling depth of between 5 and 50 Å depending upon the material being investigated and the electron kinetic energy of the emitted atomic core-level electron within the material.

Tea Bag Test Method

This test method is used to test the water absorption capacity of the porous particles with a hydrophobic shell on the exterior particle surface. The tea bag is made of nylon fabric having a mesh size of 255 (sieve opening of 57 micrometers (μm)); cut to a width of 2 inches (5.08 cm) and a length of 6 inches (15.24 cm); and folded to make a 2 inch (5.08 cm) by 3 inch (7.62 cm) tea bag. The sides of the tea bag were heat sealed. The inner dimension of the tea bag was 1.5 inches (3.81 cm) by 3 inches (7.62 cm). The following steps were used to carry out the Tea Bag Test Method:

1. Put 400 mL deionized (DI) water in a cup at room temperature (75° F. or about 23.9° C.).
2. Load 2 grams of the porous particles into the tea bag.
3. Dip the tea bag into the DI water cup and hold for 3 minutes.
4. Pull out the tea bag and drain for 1 minute.
5. Then measure the wet weight of the bag with the porous particles.
6. Repeat the test procedure (steps 1-5) without loading porous particles in the tea bag to obtain the wet weight of the tea bag.
7. Then measure the "wiped weight" after removing the water between the particles by "wiping" to remove entrained water (i.e. squeezing the particle loaded tea bag between two tetra-folded paper towels).
8. Calculate the water absorption capacity using the following equation:

Water absorption capacity (g/g)=(wiped weight of wet tea bag with particles−wiped weight of wet tea bag without particles−dry particle weight)/dry particle weight.

9. Complete three replicates of steps 1-8 for each sample.

Ammonia Odor Test

The Ammonia Odor Test was carried out on some of the samples. One gram of treated or untreated activated carbon was first placed in a 2 inch diameter plastic cup (5.08 cm). Then the particle loaded cup was placed in an 8-oz widemouth glass jar. Five milliliters of 0.1 wt % ammonium hydroxide solution was added by pipette into the wide-mouth glass jar against the inner wall to make sure the solution did not touch the particles.

The Ammonia Odor Test was conducted using Drager tubes to measure the concentration of ammonia vapor after allowing 30 minutes for the particles to adsorb the ammonia vapor produced by the ammonium hydroxide solution. Both dry and wet samples were tested. The wet samples were subjected to the Tea Bag Test using one gram of the dry porous particles placed in the tea bag. The particle-loaded tea bag was dipped into a 0.9 wt % saline solution for three minutes. Then the tea bag was pulled out of the saline solution and drained for one minute. After "wiping" to remove entrained water (i.e., squeezing the particle loaded tea bag between two tetra-folded paper towels), the wiped the samples were collected for use as the wet samples in the ammonia odor test.

Porous Particle Treatment Process 1 Examples

Porous particle treatment using Process 1 was used in preparing Comparative Examples 1-2, Examples 1-20, and Illustrative Examples 1-4.

Examples 1 to 4

A commercial parallel-plate capacitavely coupled reactive ion etcher (commercially available as Model 2480 from PlasmaTherm, St. Petersburg, Fla.) was used for plasma treatments of particles. The plasma treatments occurred while the sample was in an ion sheath that was proximate an electrode. This reactor included a grounded chamber electrode and a powered electrode. The chamber was cylindrical in shape with an internal diameter of 762 mm (30 inches) and height of 150 mm (6 inches). A circular electrode having a diameter of 686 mm (27 inches) was mounted inside the chamber and attached to a matching network and a 3 kW RF power supply that was operated at a frequency of 13.56 MHz. The chamber was vacuum pumped with a Roots blower backed by a mechanical pump. Unless otherwise stated, the base pressure in the chamber was 0.67 Pa (5 mTorr). Process gases were metered into the chamber either through mass flow controllers or a needle valve. All the plasma treatments were done by placing the sample in a glass Petri dish on the powered electrode of the plasma reactor.

The plasma treatment of the silica gel was done in two separate steps. In the first step, the particles were treated in a tetramethylsilane (TMS) plasma to deposit an organosilicon layer having attached methyl groups on the outer surface of the particles. The second step was used to produce $CF_3$, $CF_2$, and CF groups on the surface using perfluoropropane plasma.

Silica gel particles (obtained from AGM Container Controls, Inc., part number: 920014) were placed in glass Petri dishes to a depth of about 0.125-0.25 inches and placed on the powered electrode of the PlasmaTherm reaction system. The chamber was evacuated to a pressure of 10 mTorr (1.3 Pa), and tetramethylsilane was introduced at a flow rate of 150 standard cubic centimeters per minute (sccm) and a plasma was generated at a power of 1000 Watts. The operation was carried out at room temperature, and the process pressure was 50 mTorr (6.7 Pa). The duration of time when the plasma was on during the first step was 10 minutes, after which the gas was shut down, the chamber vented, and the particles manually blended in the Petri dishes.

The chamber was pumped again back down to less than 10 mTorr (1.3 Pa). Subsequently the tetramethylsilane vapor was reintroduced at a flow rate of 150 sccm (standard cc [mL] per minute), and the plasma was ignited and sustained at 1000 watts of power for another 10-minute time period. After this, the chamber was vented again, desiccant particles manually blended, the chamber pumped down, the tetramethylsilane vapor reintroduced, and the plasma sustained for a final 10-minute time period. The total time period of plasma treatment with tetramethylsilane vapor was 30 minutes.

After the end of the third plasma treatment with tetramethylsilane vapor, perfluoropropane ($C_3F_8$) gas was introduced into the chamber at a flow rate of 150 sccm and plasma reignited and sustained at 1000 watts for 10 minutes. The process pressure was 50 mTorr (6.7 Pa). After this, the gas was shut down and the chamber vented to atmosphere. The $C_3F_8$ plasma was repeated two more times with stirring of the particles in the Petri dishes by hand in between the 10-minute $C_3F_8$ plasma treatment steps. The total time for the $C_3F_8$ plasma treatment was therefore also 30 minutes.

Examples 2 to 4 were each prepared according to the method of Example 1 except using the total plasma treatment time indicated in Table 1, below. For each of Examples 2 to 4, the plasma was again ignited three times of equal, but the time period for sustaining the plasma was altered to give the total treatment time shown in the table. Each of Examples 1 to 4 was stored in a glass jar to avoid absorbing moisture before testing. Each of Examples 1 to 4 passed the Flotation Test Method, described in the Test Methods section above, with the percentage of floating particles provided in Table 1, below.

TABLE 1

| Example | TMS Time (minutes) | $C_3F_8$ Time (minutes) | Percentage of Floating Particles |
|---|---|---|---|
| 1 | 30 | 30 | 98-99% |
| 2 | 15 | 15 | 98-99% |
| 3 | 15 | 6 | 98-99% |
| 4 | 45 | None | 98-99% |

ESCA Analysis to Determine the Composition of the Surface Hydrophobic Coating

Examples 1 to 4 were evaluated using ESCA according to the test method described above. The thicknesses of the hydrophobic surface treatments on the exterior surfaces of the porous particles obtained using Process 1 were determined to be approximately 5 nm using depth profiling. The results are shown in Table 2, below.

TABLE 2

| | Atom Percentage (%) | | | | |
|---|---|---|---|---|---|
| | Untreated | Ex. 1 | Ex. 2 | Ex. 3 | Ex. 4 |
| C | 7.8 | 45.7 | 47.0 | 63.7 | 64.3 |
| O | 61.7 | 3.6 | 10.4 | 15.0 | 10.0 |
| Si | 30.7 | | | | |
| F | | 49.3 | 37.0 | 13.0 | |
| Ba | 0.1 | | | | |
| N | | 0.5 | 0.6 | 0.5 | |

Examples 1 to 3, untreated silica gel, a SAP (obtained from Sumitomo Seika, Osaka, Japan, under the trade designation "AQUA KEEP SA60S"), and wood pulp removed from a sanitary napkin obtained from Unicharm Corp. under the trade designation "BODYFIT" were evaluated using the Water Vapor Uptake Test Method described above. The results are shown in Table 3, below.

TABLE 3

| Time | Weight Increase (g/2 g) | | | | | |
|---|---|---|---|---|---|---|
| (hr) | Untreated | Ex. 1 | Ex. 2 | Ex. 3 | SAP | Pulp |
| 0.00 | 0.00 | 0.00 | 0.00 | 0.00 | 0.00 | 0.00 |
| 1.13 | 0.23 | 0.11 | 0.16 | 0.15 | 0.05 | 0.05 |
| 2.22 | 0.31 | 0.23 | 0.27 | 0.27 | 0.07 | 0.06 |
| 3.30 | 0.41 | 0.31 | 0.36 | 0.34 | 0.10 | 0.07 |
| 4.50 | 0.47 | 0.40 | 0.43 | 0.42 | 0.12 | 0.08 |
| 5.67 | 0.51 | 0.46 | 0.44 | 0.44 | 0.14 | 0.08 |
| 6.80 | 0.54 | 0.48 | 0.45 | 0.47 | 0.16 | 0.08 |
| 20.60 | 0.59 | 0.51 | 0.44 | 0.50 | 0.21 | 0.19 |
| 24.00 | 0.59 | 0.50 | 0.44 | 0.50 | 0.22 | 0.19 |

*a*The times measured for SAP and Pulp were 0, 1.03, 2.07, 3.13, 4.17, 5.33, 6.42, 22.6, and 23.63 hours.

Examples 5 and 6

For both Examples 5 and 6, silica gel particles (obtained from AGM Container Controls, Inc., part number: 920014) were treated using the following plasma treatment method that allowed for mixing during the plasma treatment process. The chamber was constructed from stainless steel and contained a horizontal mixing paddle that continuously rotated at a speed of 6 revolutions/minute (rpm). The chamber was connected to a root blower (Leybold, Model WSU 150) backed by a dry mechanical pump (Edwards, Model DP40) through a cyclone separator and particle filter. A rectangular electrode, 8.5 inches (21.6 cm) by 15 inches (38.1 cm) was located above the silica gel particle bed and connected to a 40 kHz generator (Advanced Energy, Model PE5000) to generate the plasma. Approximately 1 cubic foot (5 kg) of particles were loaded into the chamber and the chamber pumped down to a base pressure below 200 mTorr (26.7 Pa).

The plasma treatment was performed in two steps with tetramethylsilane and perfluoropropane plasmas sequentially as in Example 1, except that the mixing of the particles was done continuously during the plasma treatment step. First, tetramethylsilane vapor was introduced into the chamber at a flow rate of 300 standard cubic centimeters per minute (sccm), and the plasma was ignited and sustained at 500 watts of power for 4 hours. After this, the tetramethylsilane vapor flow was terminated and the perfluoropropane flow established at 300 sccm. The plasma was once again ignited and sustained at a power of 500 watts for another two hours with the perfluoropropane gas. For both tetramethylsilane and perfluoropropane, the pressure during the plasma treatment was in the order of 500 to 1000 mTorr (66.7 to 133 Pa). Each of Examples 5 and 6 passed the Flotation Test Method described above, with the visually estimated amount of floating particles being 90%.

Examples 1 to 3 and 5, untreated silica gel, a SAP (obtained from Sumitomo Seika under the trade designation "AQUA KEEP SA60S"), and wood pulp removed from a sanitary napkin obtained from Unicharm Corp. under the trade designation "BODYFIT" were evaluated using the Liquid Water Uptake Test Method described above. The results are shown in Table 4, below.

TABLE 4

| Water Uptake (grams) | | | | | | |
|---|---|---|---|---|---|---|
| SAP | Pulp | Untreated | Ex. 1 | Ex. 2 | Ex. 3 | Ex. 5 |
| 9.97 | 9.80 | 1.10 | 0.37 | 0.60 | 0.70 | 0.62 |

Example 7

Example 7 was prepared as described in Examples 5 and 6 except tetramethylsilane vapor was introduced into the chamber at a flow rate of 360 sccm, and the plasma was ignited and sustained at 500 watts of power for 60 minutes. No perfluoropropane gas was introduced. Example 7 passed the Flotation Test Method, described in the Test Methods section above, with 90% of the particles floating.

Illustrative Example 1 and Examples 8 to 10

Silica gel particles (obtained from AGM Container Controls, Inc., part number: 920014) were treated using the apparatus 300 shown in FIG. 3A or 3C. The particle agitator 320 was a hollow cylinder (6 cm long×5.5 cm diameter horizontal) with a rectangular opening 328 (4.5 cm×3.5 cm) at the top. The agitator 320 was fitted with a shaft 326 aligned with its axis. The shaft had a rectangular cross section (1 cm×1 cm) to which are bolted four rectangular blades 322 which form a paddle wheel for the particles being tumbled. The blades each contained two holes 324 to promote communication between the particle volumes contained in each of the four quadrants formed by the blades and agitator cylinder. The dimensions of the blades were selected to give side and end gap distances of 4 mm with the agitator walls. The particle agitator had a gas inlet port 330 at the bottom of the cylinder. The particle agitator 320 was placed in a vacuum chamber 340 connected to a mechanical pump 350 (obtained from Welch Vacuum Technology, Niles, Ill., under the trade designation "WELCH 1374 Mechanical Vacuum Pump").

Two liquid holder assemblies 360 were used to deliver vapor from the liquid source to the vacuum chamber, one for dichlorodimethylsilane (DDMS) and a second for de-ionized (DI) water. Each liquid holder assembly was made from a vacuum compatible glass tube 362, 364 (obtained from MDC Vacuum Products, Hayward, Calif.) sealed off at one end and an attached valve 366 (obtained from Swagelok Company, Solon, Ohio) to control the on/off of the vapor source.

Silica gel particles were dried in an oven set to a temperature of 155° F. (68° C.) overnight (i.e., more than 12 hours). 100 grams of the oven-dried silica gel particles were placed in the particle agitator and the chamber was pumped down to 500 mTorr (66.7 Pa) or less using pump 350. The pressure was measured by a convectron pressure gauge mounted on the chamber. The chamber was disconnected from the vacuum pump by closing the chamber valve. The valve connected to the DI water source was opened to let water vapor inside the chamber. After the chamber pressure reached 4-5 Torr (533-667 Pa), the valve was closed.

The particle agitator shaft was rotated at about 2 rpm. The silica gel particles were exposed to water vapor for 20 minutes. After 20 minutes of water vapor exposure the chamber was pumped down to 1 Torr (133 Pa) or less with the particle agitation. The DDMS valve was then opened. DDMS has a vapor pressure of 135 Torr ($1.8 \times 10^4$ Pa) at 25° C., so the liquid source did not need any external heating. In 30 seconds chamber pressure reached 3 Torr (400 Pa), and the DDMS valve was closed. The silica gel particles were exposed to varying amounts of time to DDMS vapor in the chamber by constant rotation of the agitator shaft. After the desired treatment time, the chamber was evacuated and exposed to water vapor again for 2 minutes to remove any remaining DDMS vapors. The chamber was again evacuated and vented to ambient conditions after stopping the agitation process.

For Illustrative Example 1 and Examples 8, 9, and 10, the exposure time to DDMS vapor was 5, 10, 15, and 20 minutes, respectively. Each of Illustrative Example 1 and Examples 8 to 10 were dried in oven at 155° F. (68° C.) overnight and stored in a glass jar to avoid absorbing moisture before evaluation.

Illustrative Example 1 and Examples 8 to 10 were evaluated using the Flotation Test Method described above. For Illustrative Example 1, 40 to 50% of the treated particles floated. For Examples 8 and 9, 70-80% of the treated particles floated, and for Example 10, 90% of the treated particles floated.

Illustrative Example (Ill. Ex.) 1 and Examples 8 to 10 were evaluated using ESCA according to the test method described above. The results are shown in Table 5, below.

TABLE 5

| | Atom Percentage (%) | | | | |
|---|---|---|---|---|---|
| | Untreated | Ill. Ex. 1 | Ex. 8 | Ex. 9 | Ex. 10 |
| C | 7.8 | 12.0 | 23.3 | 17.0 | 16.7 |
| O | 61.7 | 54.0 | 44.3 | 48.3 | 49.3 |
| Si | 30.7 | 33.0 | 31.3 | 34.3 | 33.0 |
| F | | | 0.4 | | |
| Ba | 0.1 | 0.1 | 0.1 | 0.1 | 0.1 |
| Cl | | 0.3 | 0.5 | 0.5 | 0.6 |

Illustrative Examples 2 and 3 and Examples 11 and 12

Illustrative Examples 2 and 3 and Examples 11 and 12 were prepared using the general method of Illustrative Example 1 and Examples 8 to 10 with the following modifications. A single layer of the oven-dried silica gel (40 grams) was placed in an aluminum tray, which was placed in a humidity chamber at 30° C. and 80% relative humidity for various times shown in Table 6, below, before a 5-minute DDMS vapor treatment. No water vapor was used during the particle agitation and treatment. The time of the humidity exposure and the weight of the silica gel before and after the humidity exposure process are shown in Table 6, below.

TABLE 6

| | Ill. Ex. 2 | Ill. Ex. 3 | 11 | 12 |
|---|---|---|---|---|
| Exposure Time to Humidity Before DDMS Treatment (minutes) | 5 | 10 | 15 | 30 |
| Particle Weight Before Humidity Exposure (grams) | 40.7 | 38.6 | 41.5 | 42.0 |

TABLE 6-continued

|  | Ill. Ex. 2 | Ill. Ex. 3 | 11 | 12 |
|---|---|---|---|---|
| Particle Weight After Humidity Exposure (grams) | 43.6 | 44.0 | 48.3 | 53.5 |
| Moisture Gain Before DDMS Treatment (grams) | 3.0 | 5.4 | 6.9 | 11.6 |
| Moisture Gain Before DDMS Treatment (%) | 7.3 | 13.9 | 16.6 | 27.6 |

Each of Illustrative Examples 2 and 3 and Examples 11 and 12 was dried in oven at 155° F. (68° C.) overnight and stored in a glass jar to avoid absorbing moisture before evaluation. Illustrative Examples 2 and 3 and Examples 11 and 12 were evaluated using the Flotation Test Method described above. For Illustrative Example 2, 30-40% of the treated particles floated. For Illustrative Example 3, 50-60% of the treated particles floated. For Example 11, 80% of the treated particles floated, and for Example 12, 90% of the treated particles floated.

Illustrative Examples 2 and 3 and Examples 11 and 12 and untreated silica gel were evaluated using the Water Vapor Uptake Test Method described above with the modification that the evaluation was carried out at 30° C. and 80% relative humidity. The results are shown in Table 7, below.

TABLE 7

| Time | Moisture Gain (g/2 g) | | | | |
|---|---|---|---|---|---|
| (hr) | Untreated | Ill. Ex. 2 | Ill. Ex. 3 | Ex. 11 | Ex. 12 |
| 0 | 0.00 | 0.00 | 0.00 | 0.00 | 0.00 |
| 1 | 0.75 | 0.67 | 0.65 | 0.62 | 0.62 |
| 2 | 0.77 | 0.70 | 0.67 | 0.63 | 0.63 |
| 3 | 0.78 | 0.70 | 0.67 | 0.63 | 0.63 |

Illustrative Examples 2 and 3 and Examples 11 and 12, untreated silica gel, a SAP (obtained from Sumitomo Seika under the trade designation "AQUA KEEP SA60S"), and wood pulp removed from a sanitary napkin obtained from Unicharm Corp. under the trade designation "BODYFIT" were evaluated for water uptake using the test method described above. The results are shown in Table 8, below.

TABLE 8

| Water Uptake (grams) | | | | | |
|---|---|---|---|---|---|
| SAP | Pulp | Untreated | Ill. Ex. 2 | Ill. Ex. 3 | Ex. 11 | Ex. 12 |
| 9.97 | 9.80 | 1.10 | 0.74 | 0.66 | 0.61 | 0.49 |

Illustrative Example 4 and Examples 13 to 15

Illustrative Example 4 and Examples 13 to 15 were prepared using the general method of Illustrative Example 1 and Examples 8 to 10 with the following modifications. A single layer of oven-dried silica gel (50 grams) was placed in an aluminum tray, and then exposed to 30° C. and 80% relative humidity for various times shown in Table 9, below before a 15-minute DDMS vapor treatment. No water vapor was used during the particle agitation and treatment. The time of the humidity exposure and the weight of the silica before and after the humidity exposure process are shown in Table 9, below.

TABLE 9

|  | Ill. Ex. 4 | Ex. 13 | Ex. 14 | Ex. 15 |
|---|---|---|---|---|
| Exposure Time to Humidity Before DDMS Treatment (minutes) | 5 | 10 | 15 | 30 |
| Particle Weight Before Humidity Exposure (grams) | 49.4 | 50.2 | 49.9 | 49.7 |
| Particle Weight After Humidity Exposure (grams) | 52.2 | 56.0 | 57.9 | 62.6 |
| Moisture Gain Before DDMS Treatment (grams) | 2.9 | 5.7 | 8.1 | 12.9 |
| Moisture Gain Before DDMS Treatment (%) | 5.8 | 11.4 | 16.2 | 25.9 |

Each of Illustrative Example 4 and Examples 13 to 15 were dried in oven at 155° F. (68° C.) overnight and stored in a glass jar to avoid absorbing moisture before evaluating.

Illustrative Example 4 and Examples 13 to 15 were evaluated using the Flotation Test Method described above. For Illustrative Example 4, 30-40% of the treated particles floated. For Examples 13 and 15, 95% of the treated particles floated, and for Example 14, 90% of the treated particles floated.

Illustrative Example 4 and Examples 13 to 15 and untreated silica gel were evaluated using the Water Vapor Uptake Test Method described above with the modification that the evaluation was carried out at 30° C. and 80% relative humidity. The results are shown in Table 10, below.

TABLE 10

| Time | Moisture Gain (g/2 g) | | | | |
|---|---|---|---|---|---|
| (hr) | Untreated | Ill. Ex. 4 | Ex. 13 | Ex. 14 | Ex. 15 |
| 0 | 0.00 | 0.00 | 0.00 | 0.00 | 0.00 |
| 1.25 | 0.77 | 0.71 | 0.70 | 0.69 | 0.65 |
| 2 | 0.77 | 0.71 | 0.70 | 0.69 | 0.65 |
| 3 | 0.77 | 0.71 | 0.70 | 0.69 | 0.65 |

Illustrative Example 4 and Examples 13 to 15, untreated silica gel, a SAP (obtained from Sumitomo Seika under the trade designation "AQUA KEEP SA60S"), and wood pulp removed from a sanitary napkin obtained from Unicharm Corp. under the trade designation "BODYFIT" were evaluated using the Liquid Water Uptake Test Method described above. The results for the Liquid Water Uptake Test Method are shown in Table 11, below.

TABLE 11

| Water Uptake (grams) | | | | | | |
|---|---|---|---|---|---|---|
| SAP | Pulp | Untreated | Ill. Ex. 4 | Ex. 13 | Ex. 14 | Ex. 15 |
| 9.97 | 9.80 | 1.10 | 0.93 | 0.61 | 0.64 | 0.60 |

Example 16

Example 16 was prepared according to the method of Illustrative Example 1 and Examples 8 to 10 except with the following modifications. Silica gel particles as received were exposed to 90° F. and 90% relative humidity for 1 hour. There was a 4.9% increase in weight. The humidified particles (100 grams) were loaded in the particle agitator and the vacuum chamber was pumped down to 10 Torr ($1.3 \times 10^3$ Pa) from the ambient 760 Torr ($1.0 \times 10^5$ Pa). After the chamber reached 10 Torr ($1.3 \times 10^3$ Pa), it was disconnected from the vacuum pump by closing the roughing valve. The particle tumbling process was initiated, and the DDMS vapor valve was opened to the agitator. After 5 minutes, the DDMS valve was closed. The chamber was evacuated for 2 minutes to remove HCl vapors and any untreated silane vapors by opening the roughing valve. Finally the chamber was vented with air and the treated sample was removed. Example 16 passed the Flotation Test Method described above, with 99% of the treated particles floating.

Illustrative Example 5

Illustrative Example 5 was prepared according to the method of Illustrative Example 1 and Examples 8 to 10 except with the following modifications. About 100 grams of as-received silica gel was loaded in the particle agitator inside the vacuum chamber. The chamber was pumped down by opening the slow roughing valve. Once the chamber pressure reached 10 Torr ($1.3\times10^3$ Pa), the chamber was disconnected by closing the roughing valve. The agitator was turned on, and the DDMS valve was open to the particles for the vapor treatment. After 5 minutes of treatment, the chamber was evacuated for 2 minutes and vented to ambient conditions. The treated particles were removed. None of the treated particles of Illustrative Example 5 floated when evaluated according to the Flotation Test Method described above.

Illustrative Example 6

Illustrative Example 6 was prepared according to the method of Illustrative Example 5 except the chamber was pumped down to 100 Torr ($1.3\times10^4$ Pa), and the DDMS treatment was carried out at 100 Torr ($1.3\times10^4$ Pa) for 5 minutes. Three percent of the treated particles of Illustrative Example 6 floated when evaluated according to the Flotation Test Method described above.

Illustrative Example 7

Illustrative Example 7 was prepared according to the method of Illustrative Example 1 and Examples 8 to 10 except with the following modifications. 100 grams of as-received silica gel was loaded in the particle agitator and placed in the vacuum chamber. The chamber was pumped down to 120 mTorr (16 Pa). At this point the chamber was isolated from the vacuum pumping system. Water vapor was admitted from the liquid water source. The particle agitator was turned on to tumble the particle bed. The chamber pressure increased to 2.50 Torr (333 Pa) from 120 mTorr (16 Pa) by filling the water vapor. The particles were tumbled for 10 minutes at this pressure by exposing to water vapor. After 10 minutes, air was let inside the chamber to increase the pressure to 10 Torr ($1.3\times10^3$ Pa). Once the chamber reached 10 Torr ($1.3\times10^3$ Pa), the vent valve was closed, and the DDMS vapor valve was open for 5 minutes to treat the particles. After 5 minutes, the chamber was pumped down for 2 minutes and vented to ambient conditions. Fifty percent of the treated particles of Illustrative Example 7 floated when evaluated according to the Flotation Test Method described above.

Illustrative Example 8

Illustrative Example 8 was prepared according to the method of Illustrative Example 1 and Examples 8 to 10 except with the following modifications. 100 grams of as-received silica gel was loaded in the particle agitator and placed in the vacuum chamber. The chamber was pumped down to 500 mTorr (67 Pa). Particle agitation was initiated, and water vapor was admitted to the chamber. The liquid water holding assembly was heated with an external heater jacket to increase the water vapor delivery to the chamber. The chamber pressure increased instantly to 11 Torr ($1.5\times10^3$ Pa) when the water boiled. At this point the DDMS valve was opened to the chamber for the treatment. After 5 minutes the chamber was evacuated for 2 minutes and vented with air. Thirty-five percent of the treated particles of Illustrative Example 7 floated when evaluated according to the Flotation Test Method described above.

Example 17

Example 17 was prepared according to the method of Illustrative Example 8 except with the following modifications. The water vapor was admitted to the chamber until the chamber reached 25 Torr ($3.3\times10^3$ Pa). After 15 minutes of exposing the silica gel particles to water vapor, the chamber was pumped down to 10 Torr ($1.3\times10^3$ Pa), and the DDMS treatment was carried out for 5 minutes at 10 Torr ($1.3\times10^3$ Pa). After the treatment the chamber was pumped out for 2 minutes and vented with air. Example 17 passed the Flotation Test Method described above, with 90% of the treated particles floating.

Illustrative Examples 5 to 8, Example 17, and untreated silica gel were evaluated using the Water Vapor Uptake Test Method described above with the modification that the evaluation was carried out at 30° C. and 80% relative humidity. The results are shown in Table 12, below.

TABLE 12

| | Moisture Gain (g/2 g) | | | | | |
|---|---|---|---|---|---|---|
| Time (hr) | Un-treated | Ill. Ex. 5 | Ill. Ex. 6 | Ill. Ex. 7 | Ill. Ex. 8 | Ex. 17 |
| 0 | 0.00 | 0.00 | 0.00 | 0.00 | 0.00 | 0.00 |
| 0.5 | 0.59 | 0.52 | 0.56 | 0.50 | 0.56 | 0.52 |
| 1 | 0.75 | 0.65 | 0.70 | 0.64 | 0.68 | 0.66 |
| 2 | 0.76 | 0.67 | 0.73 | 0.68 | 0.70 | 0.69 |
| 3 | 0.77 | 0.67 | 0.73 | 0.68 | 0.70 | 0.70 |

Illustrative Examples 5 to 8, Examples 16 and 17, and untreated silica gel were evaluated for water uptake using the test method described above with the following modification. The weight of the water that drained into the flask was not measured, but instead, the weight of the particles before and after the water exposure was measured. The difference in weight of the particles before and after water exposure is shown in Table 13, below.

TABLE 13

| | Water Uptake (grams) | | | | | |
|---|---|---|---|---|---|---|
| Untreated | Ill. Ex. 5 | Ill. Ex. 6 | Ill. Ex. 7 | Ill. Ex. 8 | Ex. 17 | Ex. 16 |
| 0.81 | 0.74 | 0.77 | 0.74 | 0.73 | 0.71 | 0.69 |

Example 18 and Comparative Example 1

Example 18 and Comparative Example 1 (C.E. 1) were prepared according to the method of Illustrative Example 1 and Examples 8-10 except with the following modifications. The as-received particles were exposed to humidity (30° C. and 80% relative humidity) before the DDMS vapor treatment. During the humidity exposure, the moisture gain of a portion of the particles was checked every 10 to 20 minutes until it reached 13.0 weight % for Example 18 and 5.9 weight % for Comparative Example 1.

About 1000 grams of the humidity-exposed silica gel were loaded in a particle agitator inside the vacuum chamber. The particle agitator was a larger version of the particle agitator used for Examples 1 to 17 and Illustrative Examples 1 to 8 with a cylinder 12 inch (30.5 cm) long having a 7 inch (17.8 cm) diameter. The cylinder had an 11.25 inch by 6.5 inch (28.6 cm by 16.5 cm) rectangular opening in the top. Each blade 322 was an 11.75 inch by 3.5 inch (29.8 cm by 8.9 cm) rectangle with holes. The chamber was pumped down to 10 Torr ($1.3 \times 10^3$ Pa). Then the agitator was turned on at 4 rotations per minute (rpm), and the DDMS valve was open to the particles for a 5-minute vapor treatment.

After the 5-minute vapor treatment, the DDMS valve was closed, and the particles were allowed to react with DDMS in the chamber for another 5 minutes. After the 10 minutes of total treatment, the chamber was evacuated for 2 minutes and vented to ambient conditions. The treated particles were removed and post-dried at 180° C. for 2 hours to remove the unreacted moisture adsorbed within the pores of the treated porous particles. Both Example 18 and Comparative Example 1 passed the Flotation Test Method described above, with greater than 95% of the treated particles floating.

Example 18, Comparative Example 1, and untreated silica gel were using the Water Vapor Uptake and Liquid Water Uptake Test Methods described above. The Liquid Water Uptake Test Method was carried out with the following modification: the weight of the water that drained into the flask was not measured, but instead, the weight of the particles before and after the water exposure was measured. When the Liquid Water Uptake Test Method was carried out, the difference in weight of the particles before and after water exposure was 0.81 grams for untreated silica gel, 0.70 grams for Example 18, and 0.61 grams for Comparative Example 1.

The Water Vapor Uptake Test Method was carried out with the following modification: the evaluation was carried out at 30° C. and 80% relative humidity. The results for water vapor uptake are shown in Table 14, below.

TABLE 14

| Time | Moisture Gain (g/2 g) | | |
|---|---|---|---|
| (hr) | Untreated | Ex. 18 | C.E. 1 |
| 0 | 0.00 | 0.00 | 0.00 |
| 0.5 | 0.59 | 0.60 | 0.55 |
| 1 | 0.75 | 0.70 | 0.71 |
| 2 | 0.76 | 0.73 | 0.73 |
| 3 | 0.77 | 0.73 | 0.73 |

Example 18, a particle similar to Example 1, and untreated silica gel were analyzed by time-of-flight secondary ion mass spectrometry (TOF-SIMS), using an instrument obtained from ION-TOF GmbH, Munster, Germany, under the trade designation "TOF.SIMS.5". The particle similar to Example 1 was prepared using the method described for Example 1 except the treatment time with TMS plasma was 60 minutes, and the treatment time with perfluoropropane plasma was 40 minutes. High mass-resolution positive and negative ion analyses were performed using a pulsed 25 keV Bi+ primary ion beam, with a beam diameter of about 3 micrometers (μm), and an analysis area of 500×500 μm. SIMS has monolayer sensitivity, with an analysis depth in the range of 10 to 20 angstroms (Å).

External surfaces of particles were analyzed by mounting a particle from each Example or untreated silica gel on double stick tape. Particle cross sections were prepared by placing individual particles under an optical microscope and splitting them with a clean razor blade. This procedure resulted in random cleavage of the particles and was sufficient to expose the interiors. Cross sections were mounted on double stick tape, with the exposed interior sitting face-up for analysis.

The external surface of the untreated silica gel particle showed characteristic SIMS silica ions: Si+, SiOH+, $SiO_2-$, $SiO_2H-$, $SiO_3-$, $SiO_3H-$, $Si_2O_5H-$, as well as other minor ions of type $Si_xO_yH_z-$. Traces of Na, Fe, Ba, hydrocarbons, S, and Cl were also present on the surface. Very little fluorine or silane or siloxane ions were observed.

The external surfaces of the particle similar to Example 1 showed numerous fluorocarbon ions, including CF+, $CF_2H+$, $CF_3+$, $C_3F_3+$, $C_2F_5+$, $C_3F_5+$, $C_3F_7+$, F-, $F_2-$, $F_2H-$, $CF_3-$, $CF_3O-$, $C_3F_3-$, $C_4F_9-$, and other minor ions of type $C_xF_y+$ and $C_xF_y-$. The level of silica ions on the surface was extremely low.

The external surfaces of Example 18 showed the same characteristic silica ions detected on the untreated silica gel particles, but additionally there were ions indicative of the silane treatment: $CH_3Si+$, $(CH_3)_3Si+$, $CH_3SiO—$, $CH_3SiO_2-$, and polydimethylsiloxane ions (117+, 133+, 147+, 207+, 221+, 281+, 325+, 149-, 223-). The chlorine level was higher than on the untreated silica gel external surface, roughly a factor of 3.

Cross sections of both the particle similar to Example 1 and Example 18 showed the same characteristic silica ions detected on the untreated silica gel external surface, with little or no fluorine or silane. The only ion on the interior which was slightly elevated in comparison to the untreated silica gel particle is F— at m/z 19 on Example 5. There were no detectable fluorocarbon ions on the interior.

To compare the treated particles in a semi-quantitative manner, the counts of various ions of representative of species of interest were ratioed to ions representative of the silica background. For the particle similar to Example 1, the ratios $CF_2+/29Si+$, $F-/SiO_2-$, and $F_2-/SiO_2-$ were selected. The results of the ion counting for the positive ions suggested that there is a decrease in F— signal going from the surface to the interior of roughly a factor of 1000. For Example 18, the ratios $CH_3Si+/SiOH+$, $[CH_3SiO—+CH_3SiO_2-]/[SiO_2H-+SiO_3-+SiO_3H-]$, and $Cl-/SiO_2-$ were selected. The results of the ion counting for the positive ions suggested that there is a decrease from surface to interior is roughly a factor of 200. There is always some background signal at every mass in SIMS, and this limits the dynamic range. Similar results were observed for the ion counting of the negative ions.

Example 19

Example 19 was prepared according to the method of Illustrative Example 1 and Examples 8 to 10 except with the following modifications. The silica gel particles were irregular shaped particles with a particle size range from 0.08 mm to 0.6 mm (obtained from AGM Container Controls, Inc., part number: 920010). The particles were white with 2.5% blue indicator. The as-received particles were exposed to humidity (30° F. and 80% relative humidity) before the DDMS vapor treatment. During the humidity exposure, the moisture gain of a portion of the particles was checked every 10 to 20 minutes until it reached 5.8 weight %. About 940 grams of the humidity-exposed silica gel was loaded in the larger particle agitator described in Example 18 inside the vacuum chamber. The chamber was pumped down to 10 Torr ($1.3 \times 10^3$ Pa).

Then the agitator was turned on at 6 rpm, and the DDMS valve was open to the particles for the vapor treatment.

During the first 10 minutes, the chamber pressure reached 11 Torr ($1.5 \times 10^3$ Pa), and 20.8 grams of DDMS were consumed. Then the DDMS valve was closed and the chamber was evacuated for 2 minutes and vented to ambient conditions. A sample of the particles was taken and evaluated using the Flotation Test Method, with 20% of the particles floating. The chamber was pumped down again to 10 Torr ($1.3 \times 10^3$ Pa). Then the agitator was turned on at 6 rpm, and the DDMS valve was open for 10 minutes to the particles for the vapor treatment. The chamber pressure reached 12.5 Torr ($1.7 \times 10^3$ Pa), and 19.3 grams of DDMS were consumed. Then the DDMS valve was closed and the chamber was evacuated for 2 minutes and vented to ambient conditions.

A sample of the particles was taken and evaluated using the Flotation Test Method, with 50% of the particles floating. The chamber was pumped down again to 10.5 Torr ($1.4 \times 10^3$ Pa). Then the agitator was turned on at 6 rpm, and the DDMS valve was open for 10 minutes to the particles for the vapor treatment. The chamber pressure reached 15.6 Torr ($2.0 \times 10^3$ Pa), and 17.2 grams of DDMS were consumed. Then the DDMS valve was closed and the chamber was evacuated for 2 minutes and vented to ambient conditions. A sample of the particles was taken and evaluated using the Flotation Test Method, with 95% of the particles floating. The treatment was stopped after a total of 30 minutes of exposure time and 57.3 grams of consumed DDMS. The treated particles were removed, sieved, and post-dried at 150° C. for 8 hours to remove the unreacted moisture adsorption in the particles.

Example 20

Example 20 was prepared according to the method of Illustrative Example 1 and Examples 8-10 except for the following modifications. The silica gel particles were white, irregular shaped particles having a particle size range from 0.2 mm to 1.0 mm (obtained from International Silica Gel Co. LTD, Shandong, China). The as-received particles were exposed to humidity (30° F. and 80% relative humidity) before the DDMS vapor treatment. During the humidity exposure, the moisture gain of a portion of the particles was checked every 10 to 20 minutes until it reached 6.0 weight %. About 1060 grams of the humidity-exposed silica gels were loaded in the particle agitator described in Example 18 inside the vacuum chamber. The chamber was pumped down to 10 Torr ($1.3 \times 10^3$ Pa). Then the agitator was turned on at 12 rpm, and a mass flow controller set at 0.7 was used as the DDMS valve.

The DDMS valve was open for 32 minutes to the particles for the vapor treatment. The chamber pressure reached 12.5 Torr ($1.7 \times 10^3$ Pa), and 32.6 grams of DDMS were consumed. Then the DDMS valve was closed, and the chamber was evacuated for 2 minutes and vented to ambient conditions. The treated particles were removed and post-dried at 150° C. for 8 hours to remove the unreacted moisture adsorption in the particles. Example 20 passed the Floatation Test Method described above, with 100% of the treated particles floating on the surface.

Comparative Example 2

About 2 kilograms of silica gel (obtained from AGM Container Controls, Inc., Tucson, Ariz., part number: 920014) was treated by using 1 liter/minute of $NF_3$ gas at a pressure of between 1 to 1.5 torr (130 to 200 Pa). Plasma was created by using a remote plasma source obtained from MKS Instruments, Wilmington, Mass., Model Astex-Astron eX. The base pressure in the chamber was below 0.1 torr (13 Pa) before introduction of the gas. The silica gel particles were treated for 30 minutes. Comparative Example 2 was subjected to the Floatation Test Method described above, with the modification that a few particles were sprinkled into a vial containing water. All of the particles sank in the water and reacted with a crackling sound.

Porous Particle Treatment Process 2 Examples

Porous particle treatment Process 2 was used in carrying out the following Example 21. The apparatus used for carrying Process 2 is generally as shown in FIG. 3A. The particle agitator was as generally shown in FIG. 3B, consisting of a hollow cylinder (6 cm long×5.5 cm diameter×horizontal length) with a rectangular opening (4.5 cm×3.5 cm) in the top. The agitator was fitted with a shaft aligned with its axis. The shaft had a rectangular cross section (1 cm×1 cm) to which was bolted four rectangular blades forming an agitation mechanism or paddle wheel for the support particles being tumbled.

The blades may optionally contain two holes to promote communication between the particle volumes contained in each of the four quadrants formed by the blades and agitator cylinder. The dimensions of the blades were selected to give side and end gap distances of 4 mm with the agitator walls. The particle agitator had a gas inlet port at the bottom of the cylinder. The particle agitator was placed in a vacuum chamber connected to a mechanical pump.

A commercially-available electro-polished stainless steel gas bubbler was used to deliver vapor from the liquid source to the vacuum chamber. The gas bubbler was a tall cylindrical sealed vessel, like those routinely used in metal organic chemical vapor deposition of thin films in semiconductor industries. The top of the bubbler had a fill port, vapor space port, and a dip tube port.

Dichloro dimethyl silane (DDMS, from Gelest, Inc., Morrisville, Pa.) was filled through the fill port of the gas bubbler, and the fill port was sealed with a metal seal plug. The valve connected to the dip port was also sealed with a metal seal plug. Only the vapor space valve was used to deliver the DDMS vapor to the vacuum particle coating system for the reaction. Additional valves were attached to control the on/off of the vapor source.

A typical method for forming a hydrophobic shell on silica gel included loading a known weight of desiccant particles in the particle agitator, and pumping the chamber down to 10-200 Torr ($1.3 \times 10^3$–$2.6 \times 10^4$ Pa) using a rotary vacuum pump. The chamber was then disconnected from the vacuum pump by closing the chamber valve. The DDMS valve was then opened to treat the particles. The initial weight of DDMS container was recorded. DDMS has high vapor pressure of 135 Torr ($1.755 \times 10^4$ Pa) at 25° C., so the liquid source did not require any external heating.

After the particles were exposed to varying amounts of time to DDMS vapor in the chamber by constant rotation of the agitator shaft the DDMS valve was closed. The final weight of the DDMS container was recorded. The difference of initial and final weight is noted as the amount of DDMS consumed for treatment of the particles. The chamber was again evacuated and vented to ambient after stopping the agitation process. The treated particles were oven dried at 150° C.

Examples 21-22 and Comparative Examples 3-4

Comparison of DDMS Treated Wide Pore (Type-B) Silica Gels Treated with Process 2

Two Type-B silica gel particles were obtained from different suppliers and treated using Process 2. One Type-B1 silica gel (CAS No: 7631-86-9; from Toyota Kako Co., Ltd.) had a larger particle size of 1-3 mm (bead shape). Type-B2 silica gel (from International Silica Gel Co., Ltd. China) had a smaller particle size of 0.5-1.5 mm (bead shape). As-received Type-B silica gel particles were first pre-humidified to 5-10 wt % by exposing the particles in a humidity oven. The particles were then loaded in the particle agitator and placed in the vacuum chamber. The description of the vacuum particle coater is described above. The vacuum chamber was then pumped down to a desired pressure. DDMS liquid was filled in a stainless steel bubbler.

The bubbler had three ports, a dip-tube, a fill port, and a vapor space. After filling the bubbler, the valve to dip tube and the fill ports were closed. Only the vapor space valve was connected to the vacuum chamber for the vapor delivery. The bubbler was maintained at ambient temperature (i.e., 22-24° C.). The process conditions are summarized in Table 15. Results of the Flotation, Liquid Water Uptake, and Tea Bag Test are summarized in Table 16.

TABLE 15

| Sample ID | Sample Weight (g) | Pre-humidity (%) | DDMS Treatment Process Pressure (Torr) | Weight of DDMS Consumed (g) | Amount of DDMS Coating (wt. %) | Particle Size (mm) |
| --- | --- | --- | --- | --- | --- | --- |
| Ex. 21 Treated Type-B1 Silica Gel | 24.96 | 6% | 10 | 2.1 | 9% | 1-3 |
| Ex. 22 Treated Type-B2 Silica Gel | 200.32 | 5% | 100 | 19.2 | 9.5% | 0.5-1.5 |
| C.E. 3 Untreated Type-B1 Silica Gel | — | 0.38% | — | — | — | 1-3 |
| C.E. 4 Untreated Type-B2 Silica Gel | — | 2% | — | — | — | 0.5-1.5 |

TABLE 16

| Sample ID | Flotation (%) | Water Uptake (g/2 g) | Tea Bag Test (g/g)* |
| --- | --- | --- | --- |
| Ex. 21 Treated Type-B1 Silica Gel | >90% | 0.39 | 0.23 |
| Ex. 22 Treated Type-B2 Silica Gel | >90% | 1.10 | 0.64 |
| C.E. 3 Untreated Type-B1 Silica Gel | 0% | 1.60 | 0.90 |
| C.E. 4 Untreated Type-B2 Silica Gel | 0% | 1.58 | 0.81 |

*One replicate only.

The results of the Water Vapor Uptake Test Method measured at 30° C. and 90% relative humidity (presented as the weight gain after moisture exposure expressed in g/g) are shown in Table 17.

TABLE 17

| Sample ID | 0.5 hr | 1.0 hr | 1.5 hr | 2.0 hr | 2.5 hr | 3.0 hr |
| --- | --- | --- | --- | --- | --- | --- |
| Ex. 21 Treated Type-B1 Silica Gel | 0.13 | 0.18 | 0.22 | 0.28 | 0.33 | 0.36 |
| Ex. 22 Treated Type-B2 Silica Gel | 0.18 | 0.25 | 0.30 | 0.35 | 0.37 | 0.39 |
| C.E. 3 Untreated Type-B1 Silica Gel | 0.26 | 0.38 | 0.48 | 0.58 | 0.66 | 0.74 |

The results indicate that for the particles treated at 100 Torr ($1.3 \times 10^4$ Pa), water vapor absorption is higher than that of the treated particles processed at 10 Torr ($1.3 \times 10^3$ Pa). The increase in absorption in less than 2 hours is preferable for personal hygiene articles. The water uptake values are significantly higher for the particles treated at 100 Torr ($1.3 \times 10^4$ Pa) compared to the 10 Torr ($1.3 \times 10^3$ Pa) treatment. These data indicate that for porous particles having a wide pore size distribution, the 100 Torr ($1.3 \times 10^4$ Pa) process pressure is desirable, although 10 Torr ($1.3 \times 10^3$ Pa) was adequate for porous particles having a narrow pore size distribution.

ESCA Analysis to Determine the Thickness of the Surface Hydrophobic Coating

ESCA was carried out on the wide pore size distribution Type-B silica gel treated at 100 Torr ($1.3 \times 10^4$ Pa) using Process 2 (Example 22). The depth profiling results showed a 45 nm thick hydrophobic coating on the exterior particle surface, leaving the interior surfaces of the pores substantially untreated and hydrophilic.

Illustrative Example 9

Process Pressure >200 Torr ($2.6 \times 10^4$ Pa)

Attempts were made to treat particles at higher pressures greater than 200 Torr ($2.6 \times 10^4$ Pa). However, the rate of delivery of DDMS vapor was significantly reduced. An external heating source may be needed to heat the DDMS bubblers to increase the vapor pressure of the liquid. In this ROI the bubbler was kept at ambient temperature and 200 Torr ($2.6 \times 10^4$ Pa) and above did not yield desired treatment in a short time.

Examples 23-25 and Comparative Example 5

Comparison of Type-B Silica Gel Porous Particles Pre-Humidified at Various Moisture Levels and Treated Using Process 2 at 100 Torr ($1.3 \times 10^4$ Pa)

A Type-B silica gel with a smaller particle size (0.5-1.5 mm bead shape from International Silica Gel Co., Ltd., China) was treated using Process 2 as described above for Example 21, using the process conditions shown in Table 18. Examples 23, 24 and 25 were treated at a process pressure of 100 Torr ($1.3 \times 10^4$ Pa) after pre-exposing the porous particles to a pre-humidity level of 46%, 1.4% and 7%, respectively. Comparative Example 5 corresponds to the untreated control sample of the Type-B silica gel at a pre-humidity level of 2%.

TABLE 18

| Sample ID | Sample Weight (g) | Pre-humidity (%) | DDMS Treatment Process pressure (Torr) | Wt. of DDMS Consumed (g) | Wt. % DDMS Coating |
|---|---|---|---|---|---|
| Ex. 23 | 125.88 | 46% | 100 | 6.8 | 8.5% |
| Ex. 24 | 76.96 | 1.4% | 100 | 10.4 | 14% |
| Ex. 25 | 85.36 | 7% | 100 | 8.0 | 10% |
| C.E. 5 Untreated Control | — | 2% | — | — | — |

The results of the Water Vapor Uptake Test Method measured at 30° C. and 90% relative humidity (presented as the weight gain after moisture exposure expressed in g/g) are shown in Table 19.

TABLE 19

| Sample ID | 0.5 hr | 1.0 hr | 1.5 hr | 2.0 hr | 2.5 hr | 3.0 hr |
|---|---|---|---|---|---|---|
| Ex. 23 | 0.12 | 0.18 | 0.23 | 0.27 | 0.31 | 0.34 |
| Ex. 24 | 0.09 | 0.14 | 0.18 | 0.21 | 0.23 | 0.25 |
| Ex. 25 | 0.12 | 0.21 | 0.28 | 0.33 | 0.38 | 0.41 |
| C.E. 5 Untreated Control | 0.14 | 0.24 | 0.33 | 0.40 | 0.47 | 0.52 |

The results indicate that pre-humidification at levels higher than 10% have negligible impact on the hydrophobic properties of the particles. However, for particles with less than 2% pre-moisture content, the loss of water vapor storage capacity is severe, indicating quenching of hydrophilic sites inside the pores.

Porous Particle Treatment Process 3 Examples

Examples 26-27 and Comparative Example 6

Comparison of As-Received Silica Gel (w/<2% Moisture Content) Treated with DDMS Through Process 2 and Process 3 (In Situ Oligomers of DDMS)

A Type-B silica gel with a smaller particle size (0.5-1.5 mm bead shape from International Silica Gel Co., Ltd., China) was treated using Process 2 and Process 3 using the apparatus as described generally in FIGS. 3A and 3C, and using the process conditions shown in Table 20. The amount of water vapor introduced at the annular mixing nozzle 380 was used to achieve the desired dimer, trimer or higher oligomer formation before the reaction product deposited on the exterior particle surfaces.

The annular mixing nozzle 380 comprised an interior (DDMS vapor carrying) tube surrounded concentrically by an outer (water vapor carrying) tube. The outer tube had an outer diameter (O.D.) of 0.5 inches (1.27 cm), and the inner tube had an outer diameter of 0.25 inches (0.636 cm). The annular mixing nozzle 380 was connected to the bottom inlet 330 of the particle agitator through a 0.25 inch (0.636 cm) polyethylene tube. The outer tube was connected to a water vapor delivery source outside of the vacuum chamber. The process conditions are summarized in Table 20.

TABLE 20

| Sample ID | Sample Weight (g) | Pre-humidity (%) | DDMS Treatment Process Pressure (Torr) | Nitrogen Flow Rate Through Water Bubbler | Water Flow Rate (g/min) | Wt. of DDMS Consumed (g) | Wt. % DDMS Coating |
|---|---|---|---|---|---|---|---|
| Ex. 26 | 76.96 | 1.4% | 100 | — | | 10.4 | 15% |
| Ex. 27 | 75.15 | 1.4% | 100 | 2 liter/min | 0.06 | 5.2 | 7% |
| C.E. 6 Untreated Control | — | 1.4% | — | — | | — | — |

Example 26 was prepared using Process 2 after pre-exposing the porous particles to a pre-humidity level of 1.4%. Example 27 was prepared using Process 3 at a process pressure of 100 Torr ($1.3 \times 10^4$ Pa) after pre-exposing the porous particles to a pre-humidity level of 1.4%, and with a nitrogen flowrate through the gas bubbler 368 of 2 liter/min. Comparative Example 6 corresponds to the untreated control sample of the Type-B silica gel at a pre-humidity level of 1.4%. Results of the Flotation, Liquid Water Uptake, and Tea Bag Test Methods are summarized in Table 21.

TABLE 21

| Sample ID | Flotation (%) | Water Uptake (g/2 g) | Tea Bag Test (g) |
|---|---|---|---|
| Ex. 26 | <70% | 1.6 | 0.8 |
| Ex. 27 | >90% | 1.6 | 0.8 |
| C.E. 6 Untreated Control | 0% | 1.8 | 0.9 |

The results of the Water Vapor Uptake Test Method measured at 30° C. and 90% relative humidity (presented as the weight gain after moisture exposure expressed in g/g) are shown in Table 22.

TABLE 22

| Sample ID | 0.5 hr | 1.0 hr | 1.5 hr | 2.0 hr | 2.5 hr | 3.0 hr |
|---|---|---|---|---|---|---|
| Ex. 26 | 0.09 | 0.14 | 0.18 | 0.21 | 0.23 | 0.25 |
| Ex. 27 | 0.13 | 0.22 | 0.28 | 0.32 | 0.37 | 0.40 |
| C.E. 6 Untreated Control | 0.14 | 0.24 | 0.33 | 0.40 | 0.47 | 0.52 |

These results show that for the as-received silica gel with less than 2% moisture content, the DDMS vapor treatment at 100 Torr using Process 2 yielded a relatively lower quality hydrophobic coating compared to the DDMS vapor treatment at 100 Torr using Process 3. The DDMS Wt. % consumption was also significantly lower for the same material treated using Process 3 compared to Process 2. For the particles treated using Process 3, the moisture uptake after treatment is very close to that of the un-treated particles of Comparative Example 6. Therefore, an in situ reaction of DDMS with controlled flow of water vapor before reaching the particles has a significant positive effect on the ability to coat the particle exterior surfaces with the hydrophobic coating, while leaving the interior pore surfaces substantially free of the hydrophobic coating.

Examples 28-30 and Comparative Example 7

Comparison of the Effect of In Situ Water Vapor Delivery on Porous Particle Treatment Using Process 3 at Various Water Vapor Flow Rates A Type-B silica gel with a smaller particle size (0.5-1.5 mm bead shape from International Silica Gel Co., Ltd., China) was treated using Process 2 and Process 3 using the apparatus as described generally in FIGS. 3A and 3C, and using the process conditions shown in Table 20. The performance is also compared with a treatment using Process 1. The process conditions are summarized in Table 23.

TABLE 23

| Sample ID | Sample Weight (g) | Pre-humidity (%) | Process | Nitrogen Flow Rate Through Water Bubbler | Water Flow Rate (g/min) | Wt. of DDMS Consumed (g) | Wt. % DDMS Coating |
|---|---|---|---|---|---|---|---|
| Ex. 28 | 85.30 | 7% | Process 2 | 0.5 liter/min | 0.02 | 6.1 | 8% |
| Ex. 29 | 85.33 | 7% | Process 2 | 1 liter/min | 0.035 | 8.0 | 10% |
| Ex. 30 | 85.36 | 7% | Process 1 | 0 | 0 | 8 | 10% |
| C.E. 7 Untreated Control | — | 1.4% | — | | | — | — |

The results of the Flotation, Liquid Water Uptake, and Tea Bag Test Methods are summarized in Table 24.

TABLE 24

| Sample ID | Flotation (%) | Water Uptake (g/2 g) | Tea Bag Test (g) |
|---|---|---|---|
| Ex. 28 | >90% | 1.03 | 0.48 |
| Ex. 29 | >90% | 0.72 | 0.22 |
| Ex. 30 | >90% | 1.15 | 0.52 |
| C.E. 7 Untreated Control | 0% | 1.8 | 0.9 |

The results of the Water Vapor Uptake Test Method measured at 30° C. and 90% relative humidity (presented as the weight gain after moisture exposure expressed in g/g) are shown in Table 25.

TABLE 25

| Sample ID | 0.5 hr | 1.0 hr | 1.5 hr | 2.0 hr | 2.5 hr | 3.0 hr |
|---|---|---|---|---|---|---|
| Ex. 28 | 0.15 | 0.23 | 0.30 | 0.36 | 0.40 | 0.43 |
| Ex. 29 | 0.12 | 0.21 | 0.27 | 0.31 | 0.36 | 0.40 |
| Ex. 30 | 0.12 | 0.21 | 0.28 | 0.33 | 0.38 | 0.41 |

The results of the Water Vapor Uptake and Tea Bag Test Methods indicate that for wide pore porous particle desiccants that were pre-humidified to 7%, the in-situ moisture vapor delivery method has a significant positive effect in reducing the amount of water uptake, thereby facilitating control of the amount of water uptake by the treated porous particles by controlling the in situ moisture delivery rate during treatment. However, the moisture uptake appears to show only a marginal benefit for in-situ delivery.

In applications of the porous particles as desiccants for use in personal hygiene articles, the combined benefit of water uptake and moisture uptake is often desired. Process 3, with the in-situ moisture vapor delivery to form the higher oligomers of DDMS (e.g., the dimer, trimer, and the higher oligomers) shows a significant improvement in the overall effect of water uptake and moisture uptake.

Example 28 and the untreated silica gel used as the starting material for Examples 28-30 were evaluated using the Ammonia Odor Evaluation procedure described above. The procedure for evaluating wet samples was used. The results are shown in Table 26, below.

TABLE 26

| Sample | Dry Weight (g) | Wet Weight (g) | Drager Reading (ppm) | % Reduction |
|---|---|---|---|---|
| Ex. 28 | 1.0123 | 2.9456 | 22 | 78 |
| C.E. 7 Untreated Control | 1.0133 | 2.1303 | 22 | 78 |

Example 31

A Type-B silica gel with a smaller particle size (0.5-1.5 mm bead shape from International Silica Gel Co., Ltd., China) was treated using Processes 2 and 3 sequentially using the apparatus as described generally in FIGS. 3A-3C, and using the process conditions shown in Table 26.

An amount of 50.00 g of as-received Type-B silica gel was loaded into a 200 cc agitator, and the chamber was pumped down to 100 Torr ($1.3 \times 10^4$ Pa). Ethanol vapor was pre-adsorbed within the pores of the porous particles prior to exposure of the particles to DDMS using the Process 2 surface treatment. The Process 2 pressure was 100 Torr ($1.3 \times 10^4$ Pa). Ethanol vapor was admitted in to the chamber through the vapor port at the bottom of the agitator. After 10 minutes, the sample was removed from the agitator and the absorbed ethanol content was measured with the moisture balance. The ethanol content was 8.19%. An amount of 55.19 g of ethanol pre-absorbed silica gel was loaded into the 200 cc agitator and the chamber was again pumped down to 100 Torr ($1.3 \times 10^4$ Pa). The DDMS treatment was carried out using Process 3 as described above. The weight of DDMS consumed after the treatment was 5.6 g. The treated samples were unloaded and dried at 150° C. for 10 minutes. The process conditions are summarized in Table 27.

TABLE 27

| Sample ID | Pre-adsorbed With Ethanol (%) | Nitrogen Flow Rate Through Water Bubbler (std. liter/min) | Wt. of DDMS Consumed (g) | Wt. % DDMS Coating |
|---|---|---|---|---|
| Ex. 31 | 8.19 | 0.1 | 5.6 | 11.2 |

The results of the Flotation, Liquid Water Uptake, and Tea Bag Test Methods are summarized in Table 28.

TABLE 28

| Sample ID | Flotation (%) | Water Uptake (g/2 g) | Tea Bag Test (g) |
|---|---|---|---|
| Ex. 31 | 100% | 0.9252 | 0.3651 |

The results of the Water Vapor Uptake Test Method measured at 30° C. and 90% relative humidity (presented as the weight gain after moisture exposure expressed in g/g) are shown in Table 29.

TABLE 29

| Sample ID | 0.5 hr | 1.0 hr | 1.5 hr | 2.0 hr | 2.5 hr | 3.0 hr |
|---|---|---|---|---|---|---|
| Ex. 31 | 0.103 | 0.157 | 0.191 | 0.246 | 0.296 | 0.339 |

Treated Activated Carbon Using Process 2

Examples 32-33 and Comparative Examples 8-9

For Examples 32 and 33, two different activated carbon samples were used. For Particle Example 32, the activated carbon had a large particle size distribution of 12×20 mesh (1.70 mm to 0.85 mm), and for Example 33, the activated carbon had a small particle size distribution of 30×70 mesh (0.60 mm to 0.212 mm). Both of the carbon particles were obtained from Kuraray Chemical Co. LTD, Japan. Examples 32 and 33 were prepared according to the procedure of Examples 28 and 29, with the process parameters shown in Table 30, below.

TABLE 30

| Sample ID | Sample Weight (g) | Pre-Humidity (wt. %) | DDMS treatment Process Pressure, (Torr, Pa) | Nitrogen Flow rate (Std. liter/min) | Water Flow Rate (g/min) | Wt. of DDMS Consumed (g) |
|---|---|---|---|---|---|---|
| Ex. 32 | 111.11 | 10 | 10, 1300) | 0.1 | 0.001 | 10.3 |
| Ex. 33 | 102.21 | 10 | 10, 1300) | 0.1 | 0.001 | 8.1 |

Examples 32 and 33 and the untreated activated carbon used as the starting material for Examples 32 and 33 were evaluated using the Liquid Water Uptake evaluation and Tea Bag Water Uptake evaluation described above, with the exception that the Tea Bag Water Uptake evaluation was carried out with only one replicate. The results are summarized in Table 31, below.

TABLE 31

| Sample ID | Water Uptake (g/2 g) | Tea Bag Test (g/g) |
|---|---|---|
| Ex. 32 | 0.64 | 0.65 |
| C.E. 8 Untreated Control for Ex. 32 | 0.77 | 0.82 |
| C.E. 9 Untreated Control for Ex. 33 | 0.84 | 0.90 |
| Ex. 33 | 0.70 | 0.49 |

Examples 32 and 33 and the untreated activated carbon used as the starting material for Examples 32 and 33 were evaluated using the Water Vapor Uptake procedure described above except that water vapor uptake was measured at 35° C. and 85% relative humidity. Weight increases (g/g) are shown in Table 32, below.

TABLE 32

| Sample ID | 0.5 hr | 1.0 hr | 1.5 hr | 2.0 hr | 2.5 hr | 3.0 hr |
|---|---|---|---|---|---|---|
| C.E. 8 Untreated Control for Ex. 32 | 0.157 | 0.288 | 0.362 | 0.430 | 0.473 | 0.483 |
| Ex. 32 | 0.149 | 0.259 | 0.315 | 0.363 | 0.390 | 0.398 |
| C.E. 9 Untreated Control for Ex. 33 | 0.182 | 0.284 | 0.369 | 0.422 | 0.438 | 0.437 |
| Ex. 33 | 0.208 | 0.337 | 0.379 | 0.388 | 0.388 | 0.387 |

Example 33 and the untreated activated carbon used as the starting material for Example 33 were evaluated using the Ammonia Odor Evaluation procedure described. The procedures for evaluating both dry wet samples were used. The results are shown in Table 33, below.

TABLE 33

| | Sample ID | | | | |
|---|---|---|---|---|---|
| | Ex. 33 | Ex. 33 | C.E. 9 Untreated Control | C.E. 9 Untreated Control | Blank |
| Sample wt. (grams) | 1.0 | 1.0 | 1.0 | 1.0 | |
| Wet or dry? | Wet | Dry | Wet | Dry | |
| NH$_3$ Concentration (ppm) | 20 | 18 | 26 | 14 | 93 |
| Reduction From Control (%) | 78 | 81 | 72 | 85 | 0 |
| Drager Tube Scale (ppm) | 2-30 | 2-30 | 5-100 | 2-30 | 5-100 |

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g. 1 to 5 includes 1, 1.5, 2, 2.75, 3, 3.80, 4, and 5). In addition, all numbers used herein are assumed to be modified by the term 'about'. Furthermore, all publications, published patent applications and issued patents referenced herein are incorporated by reference in their entirety as needed to provide support for the presently claimed invention and to the same extent as if each individual publication or patent was specifically and individually indicated to be incorporated by reference. Various exemplary embodiments have been described. These and other embodiments are within the scope of the following claims.

The invention claimed is:

1. A method of treating a plurality of porous particles comprising:
   providing a plurality of porous particles, each porous particle having an external surface and a plurality of pores with interior pore surfaces; and
   treating the external surfaces of the porous particles by contacting and reacting the external surfaces with a hydrophobic agent formed from a vapor comprising a reactive organosilane compound having a hydrophobic group, while causing the interior pore surfaces to remain substantially free of the hydrophobic agent, wherein at least a portion of the treated external surfaces of the porous particles comprise the hydrophobic group.

2. The method of claim 1, wherein treating the external surface of the porous particle comprises forming a layer comprising silicon, hydrogen, and carbon on at least a portion of the external surface of the porous particle by plasma deposition of the reactive organosilane compound.

3. The method of claim 2, further comprising forming a layer comprising fluorine and carbon by plasma deposition of a fluorinated compound on at least the portion of the layer comprising silicon, hydrocarbon, and carbon.

4. The method of claim 1, wherein treating the external surfaces of the porous particle comprises:
   exposing the porous particles to at least one of water vapor, methanol vapor or ethanol vapor; and
   exposing the porous particles to the vapor comprising the reactive organosilane compound, which reacts to form the hydrophobic agent.

5. The method of claim 4, wherein exposing the porous particles to at least one of water vapor, methanol vapor or ethanol vapor takes place before exposing the porous particles to the vapor comprising the reactive organosilane compound.

6. The method of claim 5, wherein at least a portion of the water vapor, methanol vapor or ethanol vapor condenses within at least a portion of the plurality of pores of the porous particles, thereby at least partially occluding the interior pore surfaces, before exposing the porous particles to the vapor comprising the reactive organosilane compound.

7. The method of claim 6, further comprising substantially removing the condensed water vapor, methanol vapor, or ethanol vapor from the pores after exposing the porous particles to the vapor comprising the reactive organosilane compound, optionally wherein substantially removing the condensed water vapor, methanol vapor, or ethanol vapor from the pores is accomplished by heating the particles, exposing the particles to a vacuum, or a combination thereof.

8. The method of claim 4, further comprising exposing the porous particles to a third vapor comprising a volatile compound non-reactive with the reactive organosilane before exposing the porous particles to the water vapor and the vapor comprising the reactive organosilane compound, wherein at least a portion of the volatile compound condenses within at least a portion of the plurality of pores of the porous particles, thereby at least partially occluding the interior pore surfaces.

9. The method of claim 8, wherein the volatile compound is selected from the group consisting of molecular nitrogen, carbon dioxide, a $C_1$-$C_2$ hydrocarbon, and combinations thereof.

10. The method of claim 8, further comprising substantially removing the condensed volatile compound from the pores after exposing the porous particles to the vapor comprising the reactive organosilane compound, optionally wherein substantially removing the condensed volatile organic compound from the pores is accomplished by heating the particles, exposing the particles to a vacuum, or a combination thereof.

11. The method of claim 1, wherein at least a portion of the water vapor reacts with at least a portion of the reactive organosilane compound in a vapor phase outside of the pores of the porous particles.

12. The method of claim 11, wherein the reactive organosilane compound comprises at least two silane functional reactive groups.

13. The method of claim 12, wherein the reactive organosilane compound is selected from dichlorodimethylsilane and dichlorodiethylsilane.

14. The method of claim 1, wherein the reactive organosilane compound has a vapor pressure at 25° C. of from 133 Pa to 26,600 Pa.

15. The method of claim 1, wherein treating the external surface of the porous particle takes place at a total vapor pressure of from 1,330 to 26,600 Pa.

16. The method of claim 15, wherein the plurality of pores exhibit a median pore size of at least 1 nm and no more than 4 nm, and further wherein exposing the porous particle to the vapor comprising the reactive organosilane compound occurs at a total vapor pressure of from 1,330 to 19,950 Pa.

17. The method of claim 15, wherein the plurality of pores exhibits a median pore size of at least 4 nm and no more than 10 nanometers, and further wherein exposing the porous particle to the vapor comprising the reactive organosilane compound occurs at a total vapor pressure of from 6,650 to 26,600 Pa.

18. The method of claim 1, wherein the porous particles are selected from the group consisting of porous inorganic particles, porous organic particles, porous metal particles, porous (co)polymeric particles, porous carbon particles, porous clay particles, porous molecular sieve particles, porous zeolite particles, porous desiccant particles, and combinations thereof.

19. The method of claim 1, wherein at least a portion of the external surface of the treated porous particle comprises hydrophobic groups, the hydrophobic groups comprising at least one of alkyl or aryl groups, further wherein the alkyl and aryl groups are each optionally substituted with fluorine, and additionally wherein the interior pore surfaces are at least partially hydrophilic.

20. The method of claim 19, wherein the hydrophobic groups comprise siloxanes having alkyl groups, aryl groups, or combinations thereof.

\* \* \* \* \*